US009737209B2

(12) United States Patent
Gramatikov et al.

(10) Patent No.: US 9,737,209 B2
(45) Date of Patent: Aug. 22, 2017

(54) EYE TRACKING AND GAZE FIXATION DETECTION SYSTEMS, COMPONENTS AND METHODS USING POLARIZED LIGHT

(71) Applicant: The Johns Hopkins University, Baltimore, MD (US)

(72) Inventors: Boris I. Gramatikov, Baltimore, MD (US); David L. Guyton, Baltimore, MD (US); Kristina Irsch, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 104 days.

(21) Appl. No.: 14/889,401

(22) PCT Filed: May 15, 2014

(86) PCT No.: PCT/US2014/038265
§ 371 (c)(1),
(2) Date: Nov. 5, 2015

(87) PCT Pub. No.: WO2014/186620
PCT Pub. Date: Nov. 20, 2014

(65) Prior Publication Data
US 2016/0081547 A1    Mar. 24, 2016

Related U.S. Application Data

(60) Provisional application No. 61/823,738, filed on May 15, 2013.

(51) Int. Cl.
*A61B 3/14* (2006.01)
*A61B 3/113* (2006.01)
(Continued)

(52) U.S. Cl.
CPC ............ *A61B 3/113* (2013.01); *A61B 3/0008* (2013.01); *A61B 3/0025* (2013.01);
(Continued)

(58) Field of Classification Search
CPC ... A61B 3/0008; A61B 3/0025; A61B 3/0094; A61B 3/1015; A61B 3/1025; A61B 3/113; A61B 3/14
(Continued)

(56) References Cited

U.S. PATENT DOCUMENTS 7,280,678 B2 * 10/2007 Haven .................... A61B 3/113
348/78
2004/0103111 A1    5/2004 Miller et al.
(Continued)

OTHER PUBLICATIONS

International Search Report and Written Opinion of PCT/US2014/038265.

*Primary Examiner* — Huy K Mai
(74) *Attorney, Agent, or Firm* — Venable LLP; Henry J. Daley

(57) ABSTRACT

An eye tracking and gaze fixation detection system, includes an electronically scannable optical illumination system emits polarized near-infrared (NIR) light to a retina in an eye of a subject; an optical detection system arranged in an optical path of the NIR light after being reflected from the retina of the eye of the subject, the optical detection system providing a detection signal; and a signal processing system communicates with the optical detection system to receive the detection signal, wherein the optical illumination system emits the polarized NIR light to illuminate at least a portion of a scanning path, wherein the scanning path is a spatially closed loop across a portion of the retina in the eye of the subject that repeats periodically over time, and wherein the signal processing system is configured to determine at least
(Continued)

one of a gaze direction and a gaze fixation based on the detection signal.

28 Claims, 32 Drawing Sheets

(51) Int. Cl.
    *A61B 3/00*     (2006.01)
    *G06F 3/01*     (2006.01)
    *G06K 9/00*     (2006.01)
    *G01N 21/21*     (2006.01)
    *G01N 21/23*     (2006.01)
    *G02B 5/30*     (2006.01)
    *G02B 26/08*     (2006.01)
    *G02F 1/13*     (2006.01)
    *G02B 5/28*     (2006.01)

(52) U.S. Cl.
    CPC ........... *A61B 3/0091* (2013.01); *G01N 21/21* (2013.01); *G01N 21/23* (2013.01); *G02B 5/3016* (2013.01); *G02B 26/0833* (2013.01); *G02F 1/1313* (2013.01); *G06F 3/013* (2013.01); *G06K 9/00604* (2013.01); *G02B 5/28* (2013.01)

(58) Field of Classification Search
    USPC ................ 351/205, 206, 209, 210, 221, 246
    See application file for complete search history.

(56) References Cited

U.S. PATENT DOCUMENTS

| | | |
|---|---|---|
| 2005/0213983 A1 | 9/2005 | Shie et al. |
| 2012/0092972 A1 | 4/2012 | Taratorin et al. |
| 2012/0229768 A1 | 9/2012 | Gramatikov et al. |
| 2013/0036830 A1 | 2/2013 | Poyarkov et al. |
| 2015/0289762 A1* | 10/2015 | Popovich ........... G02B 27/0093 351/209 |

\* cited by examiner

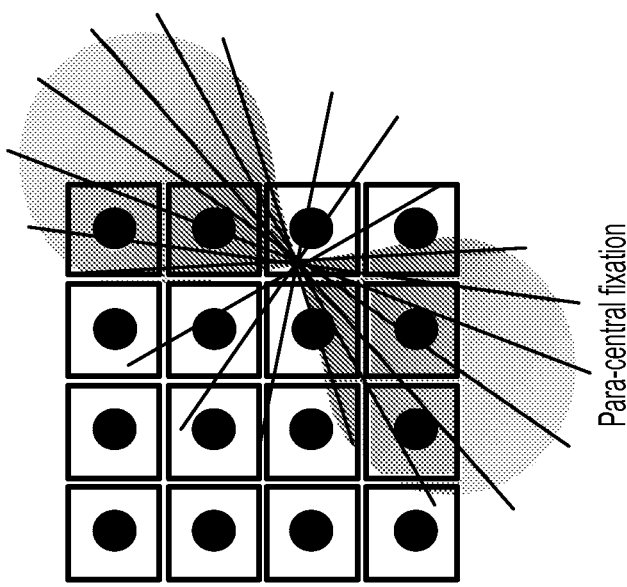
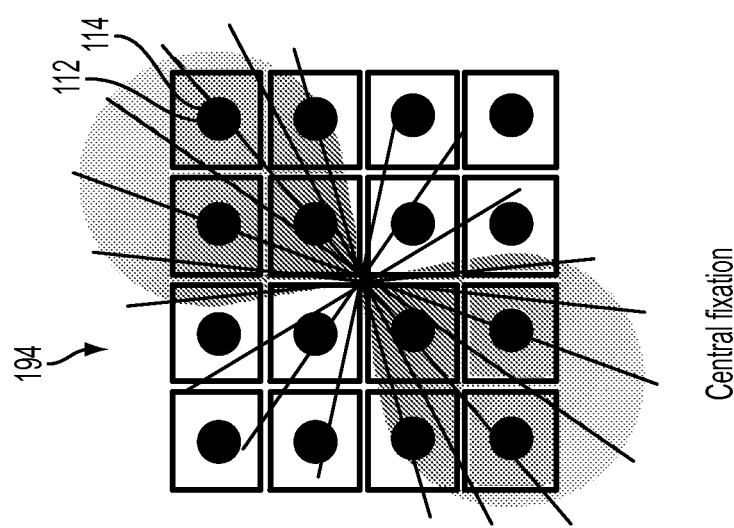
FIG. 31

EYE TRACKING AND GAZE FIXATION DETECTION SYSTEMS, COMPONENTS AND METHODS USING POLARIZED LIGHT

CROSS REFERENCE TO RELATED APPLICATIONS

This is a national stage application under 35 U.S.C. §371 of PCT/US2014/038265 filed May 15, 2014, the entire contents of which are incorporated herein by reference and this application claims priority to U.S. Provisional Patent Application No. 61/823,738, filed May 15, 2013, which is hereby incorporated herein by reference in its entirety.

TECHNICAL FIELD

The field of embodiments of this invention relates to eye tracking and gaze fixation detection systems, components and methods of eye tracking and gaze fixation detection.

BACKGROUND

There is an increasing demand for accurate portable eye trackers and fixation monitors. Since eye gaze is a strong indication for current attention and intention, such a device may automatically and accurately estimate: where the person is looking, the current and past areas of attention, the possible intentions of the person, and the possible mental state of a person. Eye tracking thus provides a key input to enable a range of applications and devices that would benefit from utilizing such information. The scope of potential applications is extensive, ranging from medical diagnostics to intuitive and fast computer interfacing. Examples include mobile devices, computer interaction in professional environments, clinical diagnostics, security applications, vehicle security and vehicle interaction, computer gaming, etc. Presently, eye tracking already provides great value in commercial and research-related applications such as psychology and vision research, commercial usability and advertising studies, and eye-based communication for people with highly limited mobility, etc.

Eye position can be estimated by a variety of techniques, each of them having its advantages and limitations. While the purpose of an eye tracker is to identify where a person is looking, most contemporary eye trackers detect eye position, usually employing the reflection of a point light source from the front of the cornea (corneal light reflex) relative to the bright or dark pupil, or relative to the reflection of the same point light source from the back of the crystalline lens of the eye (fourth Purkinje image). These and other similar techniques monitor the position of the globe itself, and not the actual visual axis or point of fixation. When an individual looks at a target, that target is imaged on the fovea. It is thus foveal fixation that correlates precisely with gaze direction. Our recent research has shown that techniques which effectively track or monitor the optical projection of fundus landmarks out from the eye afford a more direct measurement of fixation direction, are physiologically more relevant, and can achieve high precision. It has also been shown that landmarks such as the fovea and the optic disc can be detected robustly by measuring the amount of polarization change that the surrounding birefringent nerve fibers cause during double passage of a beam of polarized light through them upon fundus reflection in double-pass systems. Polarized near-infrared light is reflected from the foveal and optic disc areas in bow-tie or propeller patterns of polarization states. For any particular eye and particular type of polarized light used, the pattern of reflected polarization states is of constant shape, size, and location relative to the direction of that eye's fixation and are therefore detectable, offering the opportunity for precise eye tracking. An advantage of this new eye-fixation detection and tracking method can include that it uses true information coming directly from retinal landmarks, as opposed to existing eye-tracking systems which use reflections from other structures, to identify the direction of foveal gaze.

As noted above, while the purpose of an eye tracker is to identify where a person is looking, most contemporary eye trackers detect eye position, usually employing the reflection of a point light source from the front of the cornea (corneal light reflex) relative to the bright or dark pupil, or relative to the reflection of the same point light source from the back of the crystalline lens of the eye (fourth Purkinje image). These and other similar techniques monitor the position of the globe itself, and not the actual visual axis or point of fixation. When an individual looks at a target, that target is imaged on the fovea. It is thus foveal fixation that correlates precisely with gaze direction. We have previously developed eye fixation monitors that use foveal information, employing moving parts to scan the area around the fovea. However, moving parts can lead to cost and reliability issues, as well as difficultly in compactly incorporating such optoelectronic systems into many devices.

There thus remains a need for improved eye tracking and gaze fixation detection systems, methods and components.

SUMMARY

In one embodiment, an eye tracking and gaze fixation detection system, can include an electronically scannable optical illumination system arranged to emit polarized near-infrared (NIR) light to at least a portion of a retina in an eye of a subject; an optical detection system arranged in an optical path of said NIR light after being reflected from the retina of the eye of the subject, said optical detection system providing a detection signal; and a signal processing system configured to communicate with the optical detection system to receive said detection signal, wherein the optical illumination system is configured to emit the polarized NIR light to illuminate at least a portion of a scanning path, wherein said scanning path is a spatially closed loop across a portion of said retina in said eye of said subject that repeats periodically over time, and wherein the signal processing system is configured to determine at least one of a gaze direction and a gaze fixation based on the detection signal.

In another embodiment, a polarization-sensitive optical transducer can include a source of polarized light that has an end portion arranged to project the polarized light; a photodetector that surrounds the source of polarized light and that is in a substantially same plane as the end portion of the source of polarized light, wherein the photodetector senses light from said source of polarized light when the light strikes a polarization-changing object and is back-reflected toward said source and surrounding photodetector, wherein said polarization-sensitive optical transducer is configured to detect a polarization state of the back-reflected light, and wherein the polarization-sensitive optical transducer provides information about the polarization changing properties of said polarization-changing object based on the detected polarization state.

Additional features, advantages, and embodiments of the invention are set forth or apparent from consideration of the following detailed description, drawings and claims. Moreover, it is to be understood that both the foregoing summary of the invention and the following detailed description are examples and are intended to provide further explanation without limiting the scope of the invention as claimed.

BRIEF DESCRIPTION OF THE DRAWINGS

FIG. 31 shows 4×4 arrays of combined emitter-photodetectors, onto which the fovea is projected.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "electronically scannable" is intended to include electronic, optoelectronic and/or MEMS components that can be used to direct an NIR beam selectively spatially and temporally without the use of motors or other macroscopic mechanical components.

The term "electronically scannable optical illumination system" can be considered a solid state system in the broad sense, which can also include MEMS devices.

The term "closed loop" is not limited to any particular shape.

Figure 1:
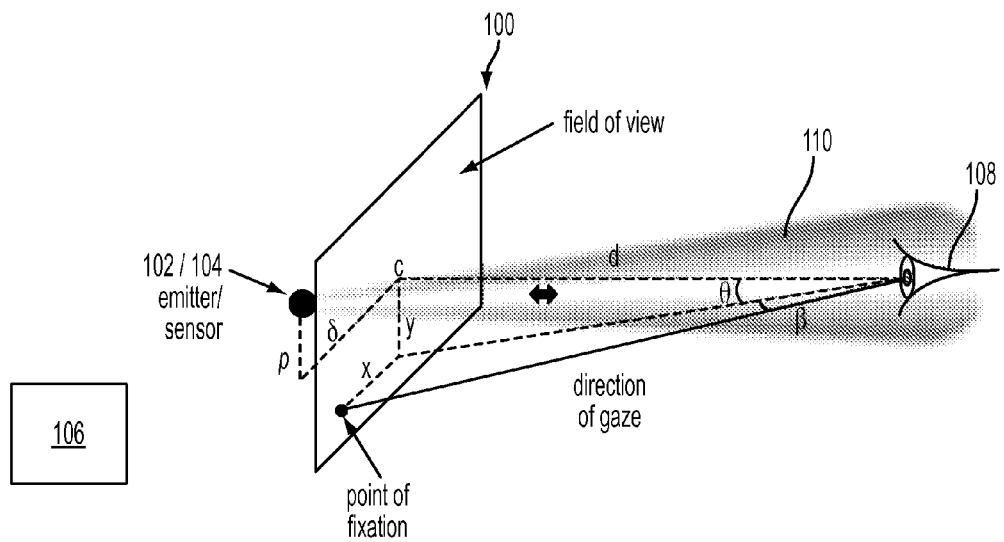
FIG. 1 shows an eye being illuminated with near-infrared (NIR) polarized light and returning light.

FIG. 1 shows an eye tracking and gaze fixation detection system 100 including an electronically scannable optical illumination system 102 arranged to emit polarized near-infrared (NIR) light to at least a portion of a retina in an eye 108 of a subject, an optical detection system 104 arranged in an optical path of the NIR light after being reflected from the retina of the eye 108 of the subject, the optical detection system 104 providing a detection signal, and a signal processing system 106 configured to communicate with the optical detection system 104 to receive the detection signal, wherein the optical illumination system 102 is configured to emit the polarized NIR light to illuminate at least a portion of a scanning path, wherein the scanning path is a spatially closed loop across a portion of the retina in the eye 108 of the subject that repeats periodically over time, and wherein the signal processing system 106 is configured to determine at least one of a gaze direction and a gaze fixation based on the detection signal. The signal processing system 106 may include includes one or more processors, such as, e.g., but not limited to, that are connected to a communication infrastructure (e.g., but not limited to, a communications bus, cross-over bar, interconnect, or network, etc.). The term signal processing system 106 may include any type of processor, microprocessor and/or processing logic that may interpret and execute instructions (e.g., for example, a field programmable gate array (FPGA)). The signal processing system 106 may comprise a single device (e.g., for example, a single core) and/or a group of devices (e.g., multi-core). The signal processing system 106 may include logic configured to execute computer-executable instructions configured to implement one or more embodiments. The instructions may reside in main memory or secondary memory. The data processor may also include multiple independent cores, such as a dual-core processor or a multi-core processor. The signal processing system 106 may also include one or more graphics processing units (GPU) which may be in the form of a dedicated graphics card, an integrated graphics solution, and/or a hybrid graphics solution. Various illustrative software embodiments may be described in terms of this illustrative computer system. After reading this description, it will become apparent to a person skilled in the relevant art(s) how to implement the invention using other computer systems and/or architectures.

Some embodiments of the current invention provide methods and compact systems with no moving parts to enable a) eye tracking without any optics between the device and the subject's eyes, and b) detecting fixation on a point source of light without calibration. A typical application for (a) would be, but is not limited to, eye tracking for computer interface (monitors), tablet devices, mobile phones, assistive devices, machine interface etc. A typical application for (b) would be, but is not limited to, pediatric vision screeners that detect central fixation, or as supplemental subsystems of ophthalmic diagnostic devices for obtaining information from the retina during central fixation, such as optical coherence tomography (OCT) devices, scanning laser ophthalmoscopes, retinal tomographs, scanning laser polarimeters, fundus cameras, and others. Other areas of application could include perimeters, or for fixation monitors for behavioral or psychological tests where deviations from steady fixation on a target are used as a differentiating measure, etc.

When the eye 108 is illuminated with near-infrared (NIR) polarized light 110, the returned light is comprised of three main components: light returned from the retina, light reflected from the cornea, and light reflected from the face. FIG. 1 shows that the magnitude and polarization signature of each of these components depends on the distance d to the eye 108, specifically with the polarization change being dependent on the position of the point of fixation (x,y), the direction of gaze ($\beta,\theta$), and the location of the electronically scannable optical illumination system 102/optical detection system 104 ($\delta,\rho$), with respect to a reference point such as the center of the field of view C.

$$S(x,y,d,\delta,\rho)=R(x,y,d,\delta,\rho)+C(x,y,d,\delta,\rho)+F(x,y,d,\delta,\rho) \quad (1)$$

Figure 2:
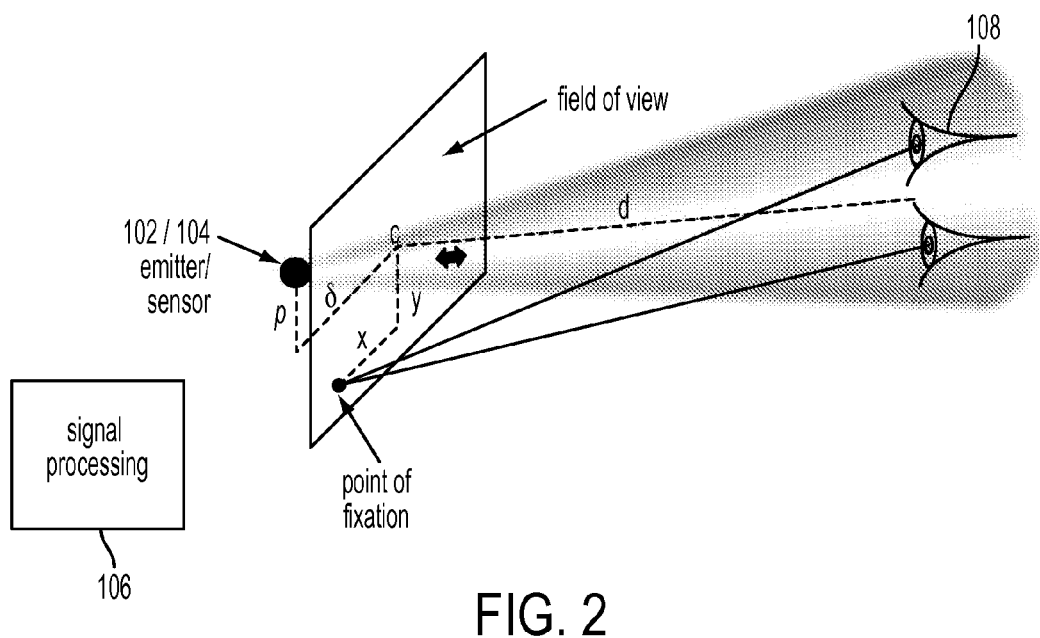
FIG. 2 shows two eyes being illuminated with NIR polarized light.

FIG. 2 shows that in a binocular configuration, each eye will contribute differently to the sum received by the sensor:

$$S=S_{RE}(x,y,d,\delta,\rho)+S_{LE}(x,y,d,\delta,\rho) \quad (2)$$

Figure 3:
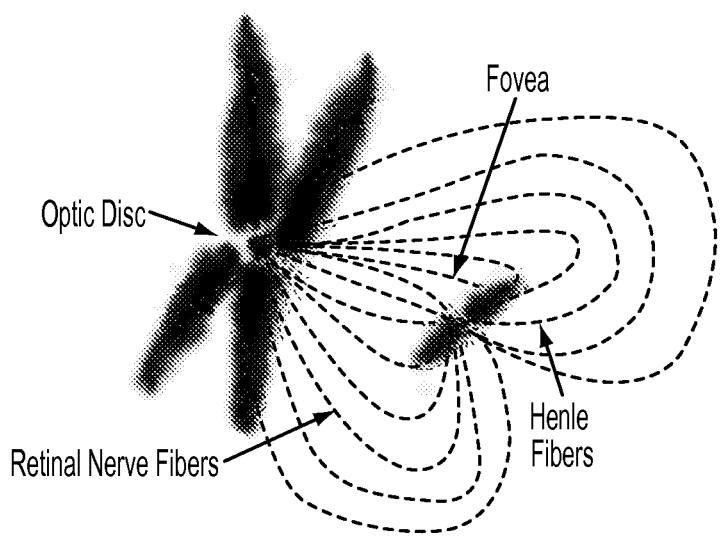
FIG. 3 shows retinal birefringence patterns of the fovea and retinal nerve fiber layers.

FIG. 3 shows that the two main birefringent structures in the retina are the Henle fiber layer centered on the fovea and the retinal nerve fiber layer (RNFL) beginning at the ganglion cells throughout the retina and thus thickening as its component nerve fibers converge to the optic disc. Physiologically, relevant to the goal of eye tracking is the information coming directly from the retina. It is related to the two-dimensional distribution of birefringence across the retina, and the particular information depends upon the exact location on the fundus that reflects the light returning to the photodetector 114 or sensor. The eye muscles rotate the eye so that the object of interest is imaged by the eye onto the fovea, which is the area of the retina with highest resolution detection.

Figure 4:
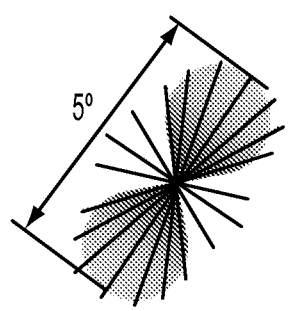
FIG. 4 shows polarized NIR light being reflected in a bow-tie pattern of polarization states.

FIG. 4 shows that polarized NIR light is reflected from the foveal area in a bow-tie pattern of polarization states due to the radial orientation of the Henle fibers. The foveal bow-tie subtends ~5° centered on the fovea, and can therefore be used for eye-tracking within this range. The visual field available for eye tracking purposes is increased by inclusion of polarization changes from the thickening retinal nerve fiber layer (RNFL) converging upon the optic disc. The visual angle between the center of the fovea (foveola) and the optic disc is about 14-15°.

Figure 5:
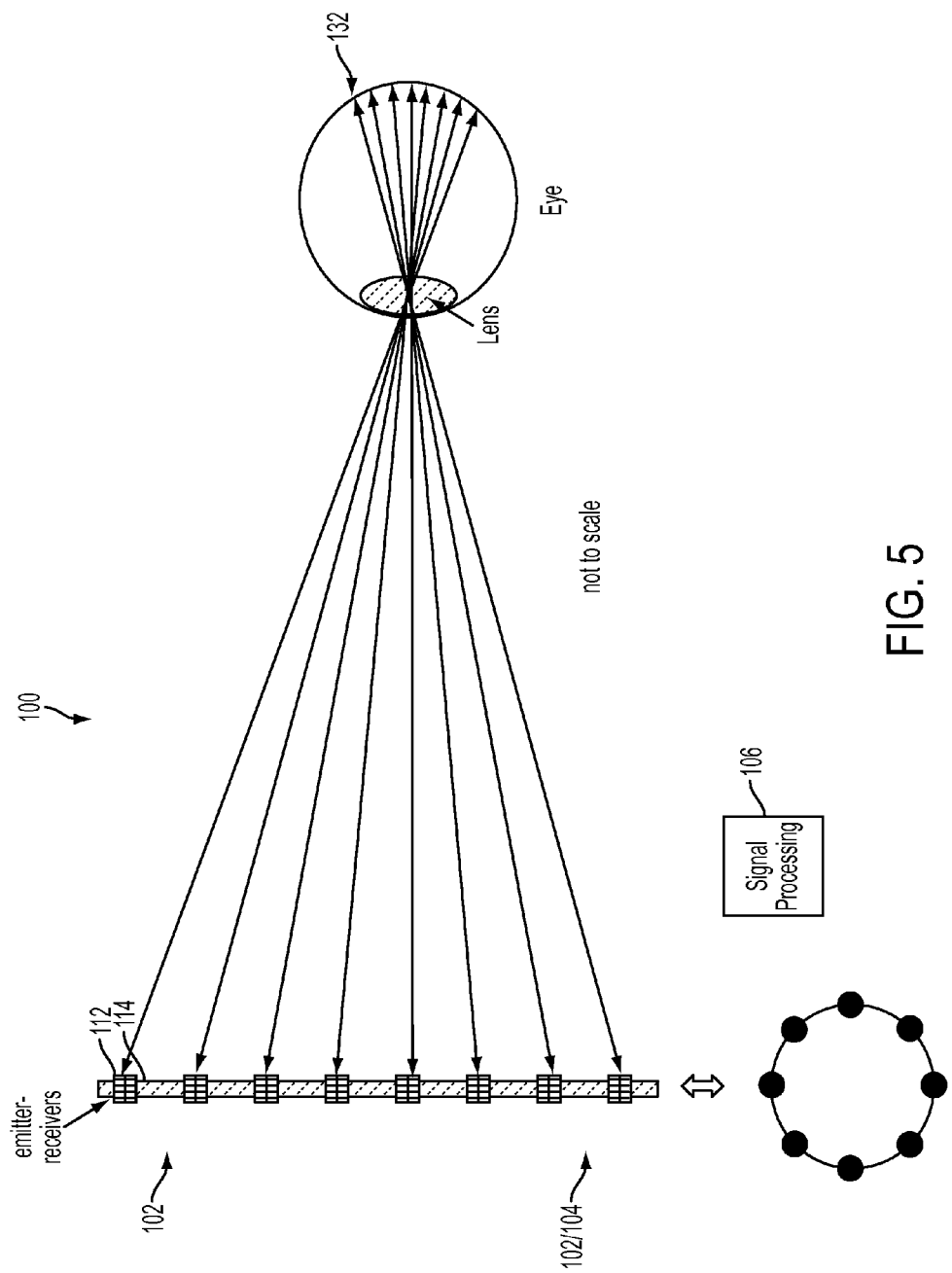
FIG. 5 shows a plurality of emitter-detectors in relation to an eye.

In FIG. 5, an eye tracking and gaze fixation detection system 100 includes an electronically scannable optical illumination system 102 that has a plurality of emitters 112 that are electronically addressable to emit in a timed sequence corresponding to portions of the scanning path. In FIG. 5, an eye tracking and gaze fixation detection system 100 includes an optical detection system 104 that includes a plurality of polarization-sensitive detectors 114 arranged at least one of substantially coincident with or optically conjugate with a corresponding one of the plurality of emitters 112 to detect the at least one polarization component of the reflected near-infrared light from the retina 132 of the eye 108 of the subject.

Some embodiments of an eye tracking system according to the current invention do not use any moving parts, and employ no optics (for the eye trackers) or only minimal optics (for the fixation monitors) between the device and the subject's eye, allowing for compact portable designs. FIG. 5 illustrates the principle of retinal eye tracking according to some embodiments of the current invention based on interrogating different points on the retina (one at a time, or in combinations) while the direction of gaze is not changing (or is relatively constant). Polarized light originating from each NIR point light source is focused by the eye's own optics (the cornea and crystalline lens) as a spot on the birefringent retina.

Figure 6:
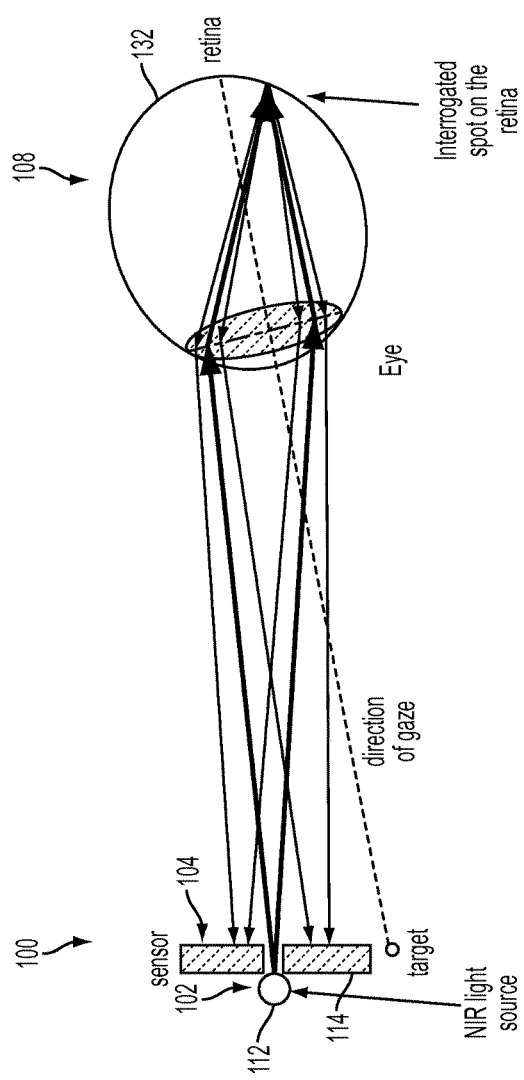
FIG. 6 shows a double-pass system for birefringence-based retinal eye tracking.

In one embodiment, a beam splitter is not necessary to separate light from the emitters to the detectors, which can allow for a compact design. This principle is shown in FIG. 6 in a double-pass system, with illustration of only a single emitter/detector pair for ease of understanding. A small portion of the light, with double passage through the corneal birefringence and birefringent nerve fibers that change its polarization state as a function of the spot's location, is retro-reflected towards the source. Because the source and the target (direction of gaze) do not coincide, and because of the imperfections in the focusing system, the returning light is slightly out-of-focus, as a result of which a large portion of it is captured by the holed sensor. By using several combinations of emitter 112 and photodetector 114, larger regions of the retina can quickly be interrogated. In systems with calibration, first a birefringence map is constructed, that is later compared with incoming measurements from the retro-reflected light, to identify which part of the map is aligned with the center of the measurement system, thus identifying the direction of gaze. In non-calibrated systems, the areas in the vicinity of specific patterns (i.e. the fovea) are interrogated, in order to identify them and estimate where they are located with respect to the middle of the viewing/measurement system. In one embodiment, the plurality of emitters 112 can comprise a laser diode. In another non-mutually exclusive embodiment, the plurality of emitters 112 can comprise a light-emitting diode. Further, each of the plurality of emitters 112 can comprise a laser diode.

Figure 7:
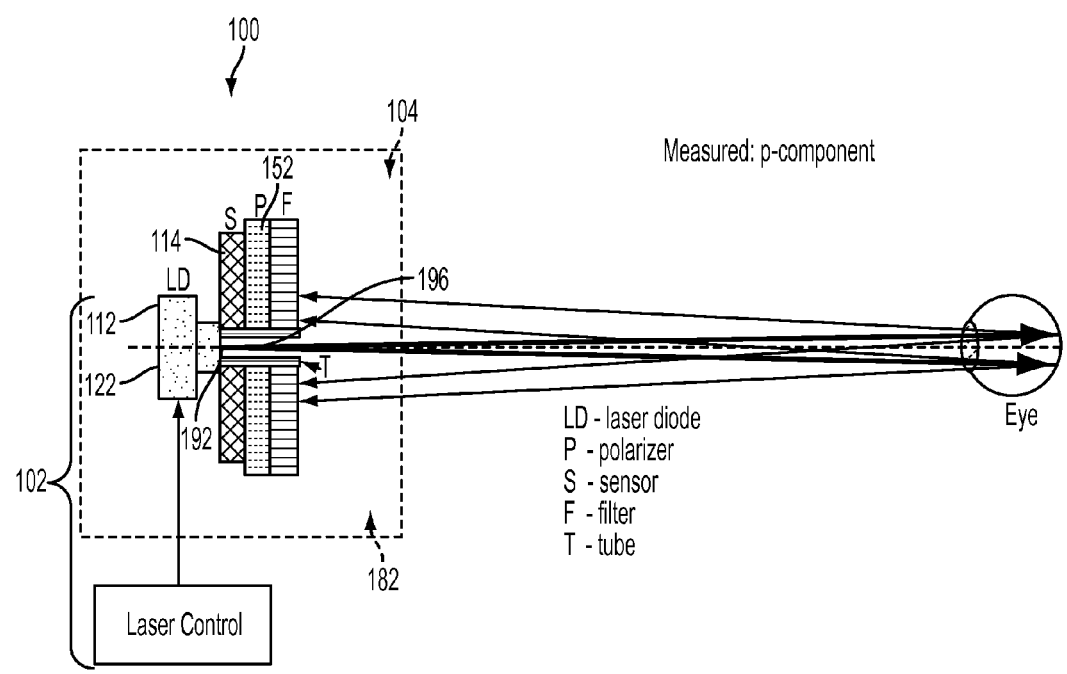
FIG. 7 shows a polarization-sensitive emitter-receiver with a laser diode.

FIG. 7 shows a polarization-sensitive optical transducer 182 eye tracking and gaze fixation detection system 100, wherein the electronically scannable optical illumination system 102 and the optical detection system 104 comprise a polarization-sensitive optical transducer 182, the polarization-sensitive optical transducer 182 including a source 184 of polarized light that has an end portion 196 arranged to project the polarized light; a photodetector 114 that surrounds the source 184 of polarized light and that is in a substantially same plane as the end portion 196 of the source 184 of polarized light, wherein the photodetector 114 senses light from the source 184 of polarized light when the light strikes a polarization-changing object and is back-reflected toward the source and surrounding photodetector 114, wherein the polarization-sensitive optical transducer 182 is configured to detect a polarization state of the back-reflected light, and wherein the polarization-sensitive optical transducer 182 provides information about the polarization changing properties of the polarization-changing object based on the detected polarization state. In one embodiment, as shown in FIG. 7, the photodetector 114 of the polarization-sensitive optical transducer 182 can include a linear polarizer 152. The polarization-sensitive optical transducer 182 can be for ocular use, for example, with polarized light and an analyzer in detecting polarization changes in the light retro-reflected from a fundus of an eye, or retro-reflected from some other polarization-changing object. In one embodiment, the transducer 182 has the distinct advantages of small size and light conservation in comparison with existing optical systems. For example, such transducers may be used to detect when an eye is even present within a defined field of view via polarization changes that are detected even with a single such module.

Figure 8:
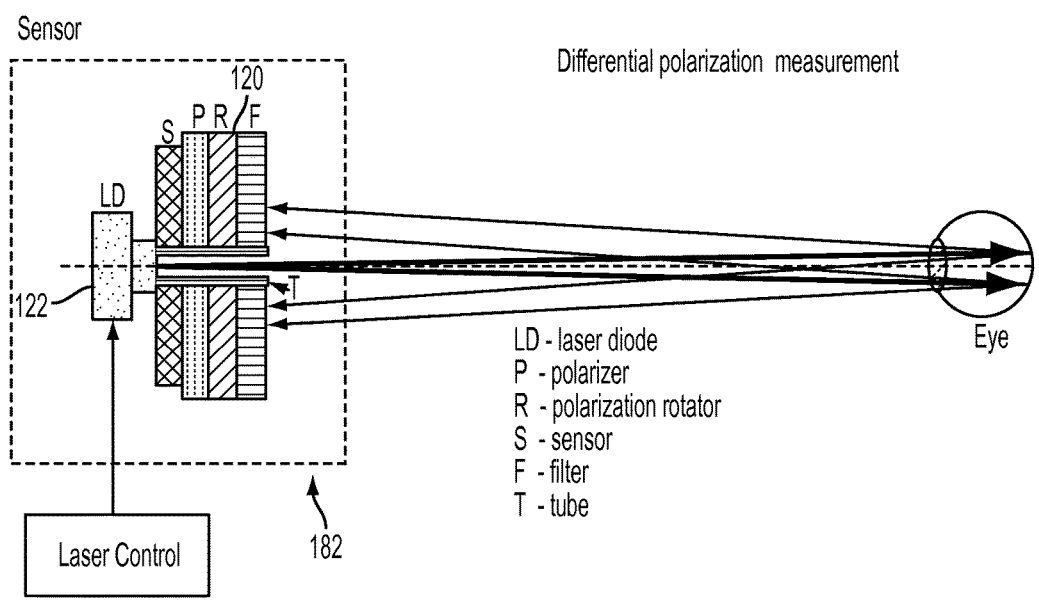
FIG. 8 shows a polarization-sensitive emitter-receiver with a polarization rotator.

FIG. 8 shows the polarization-sensitive optical transducer 182 including a photodetector 114 that has a polarization rotator 120 that is configured to rotate the polarization orientation of the back-reflected light from one meridional position to at least one other meridional position. When the rotation is 90 degrees, both the s- and p-components of the polarized light returned to the detector can be measured, for example, sequentially.

Figure 9:
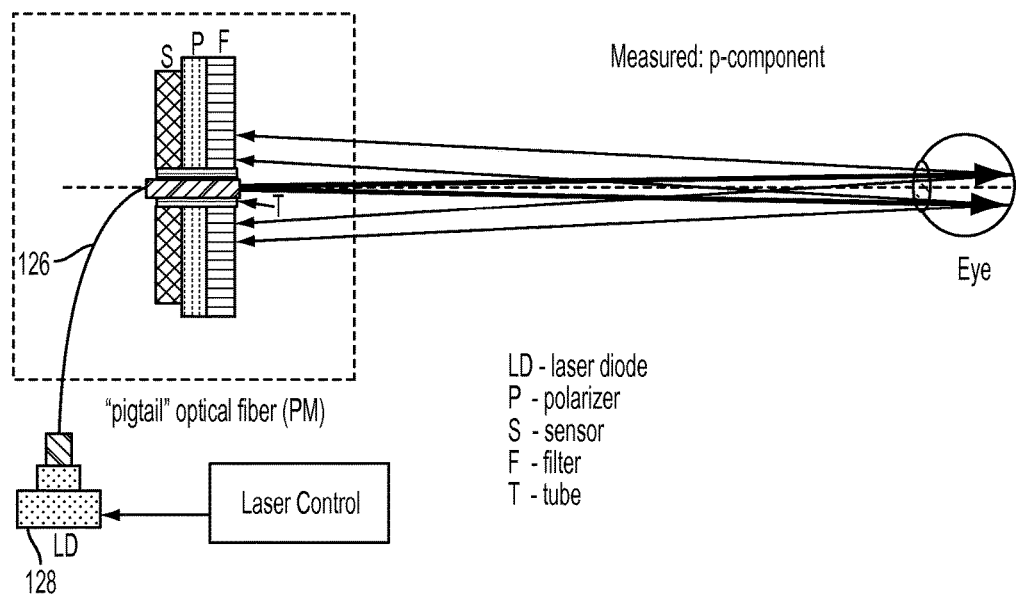
FIG. 9 shows a polarization-sensitive emitter-receiver with a pigtail optical fiber.

The laser diode 122 in the previous two examples can be replaced by a fiber-coupled laser diode 128, as seen in FIG. 9. FIG. 9 shows a polarization-sensitive optical transducer 182 wherein the source 184 of polarized light comprises a pigtail laser diode 128 having a polarization-maintaining optical fiber 126 that extends through a hole in the surrounding photodetector 114. In FIG. 9, a polarization maintaining (PM) "pigtail" optical fiber 126 delivers the light to the emitter 112/photodetector 114 combination (measurement with a simple polarizer).

Figure 10:
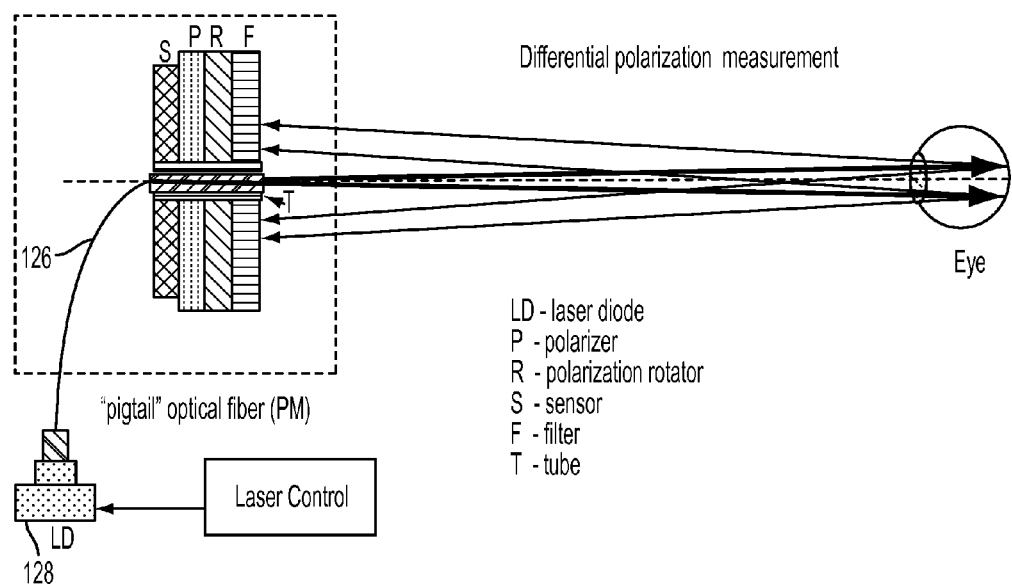
FIG. 10 shows a polarization-sensitive emitter-receiver with a polarization rotator and a pigtail optical fiber.

In FIG. 10, a PM optical fiber 126 delivers the light to the emitter/sensor combination (differential polarization measurement using a polarization rotator 120).

Figure 11:
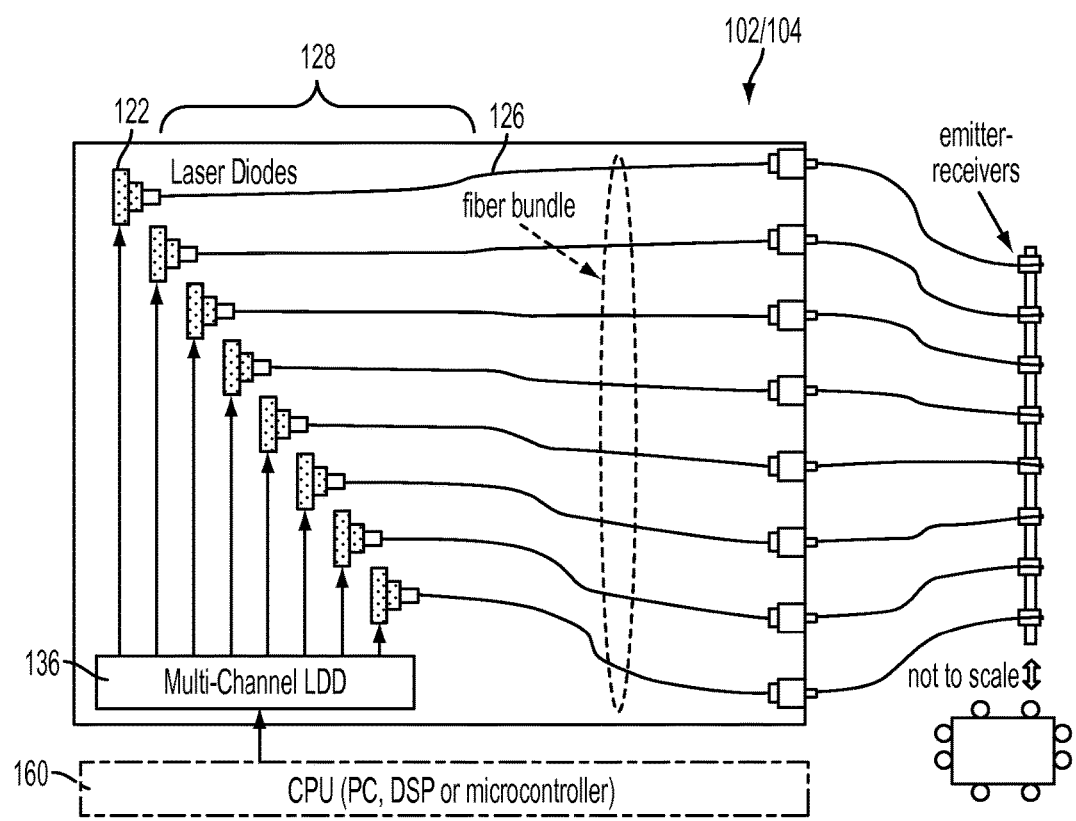
FIG. 11 shows a fiber-coupled multi-emitter/receiver using multiple laser diodes.

FIG. 11 shows a fiber-coupled solution using multiple laser diodes each with its own laser diode driver 124. Thus, FIG. 11 shows an eye tracking and gaze fixation detection system 100 where the electronically scannable optical illumination system 102 includes a plurality of PM optical fibers 126 and where each PM optical fiber 126 is optically coupled to a corresponding one of the plurality of laser diodes 122.

FIG. 11 shows a fiber-coupled multi-emitter/receiver LDD 136 using multiple fiber-coupled laser diodes 128. One embodiment can have a CPU, such as a PC, DSP or microcontroller, coupled to the multi-channel LDD 136, which is also communicatively coupled to the fiber-coupled laser diodes 128.

Figure 12:
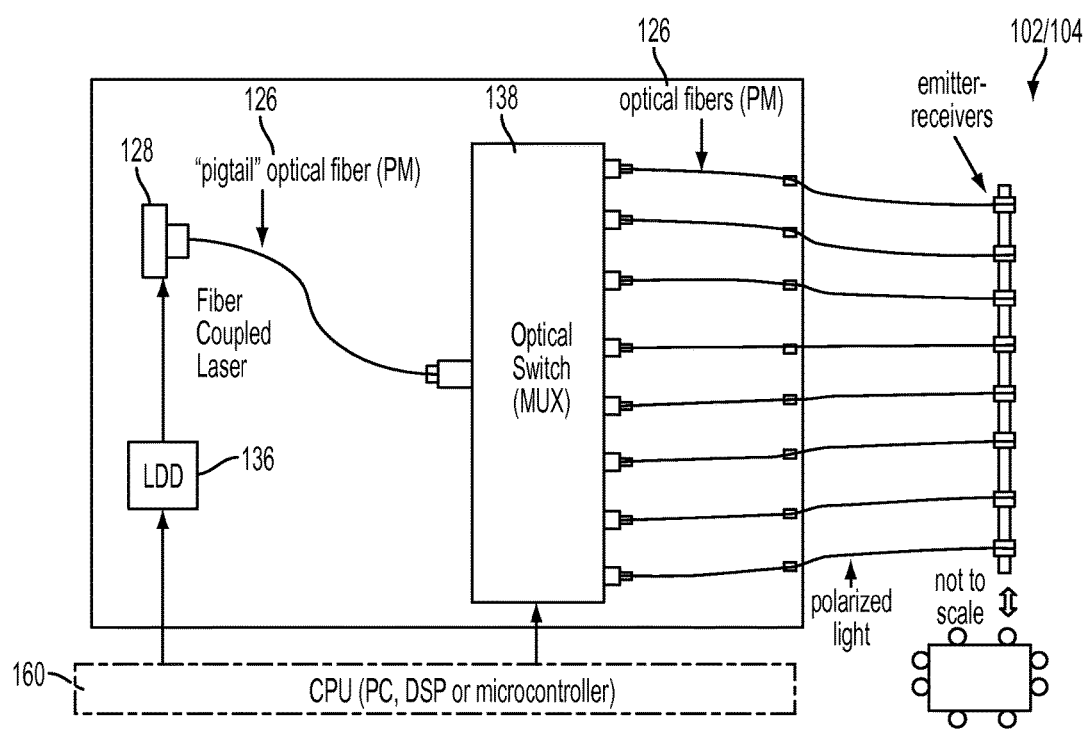
FIG. 12 shows a fiber-coupled multi-emitter/receiver using a single laser diode and an optical switch.

Fiber-coupled designs have an additional potential advantage in that they may use a single laser diode 122 coupled to an optical switch/multiplexer (optical MUX) 138, thus eliminating the need for balancing the power output from many laser diodes 122, as shown in FIG. 12. FIG. 12 shows that an eye tracking and gaze fixation detection system 100 can include an electronically scannable optical illumination system 102 that comprises a laser diode 122 coupled to an optical MUX 138, and where the optical MUX 138 is optically coupled to each of the plurality of emitters 112 within electronically scannable optical illumination system 102. In contrast to other differential polarization measurement systems, one embodiment can measure returning light of changed polarization without losses usually incurred by a non-polarizing beam splitter used to introduce the source of light into the common light path. Another embodiment is an eye tracking and gaze fixation detection system 100 where each of the plurality of emitters comprises an LED and where the electronically scannable optical illumination system 102 comprises a polarizer disposed in an optical path between the emitter 112 and the subject and also comprises an optical MUX 138 that is optically coupled to the plurality of emitters 112.

Figure 13:
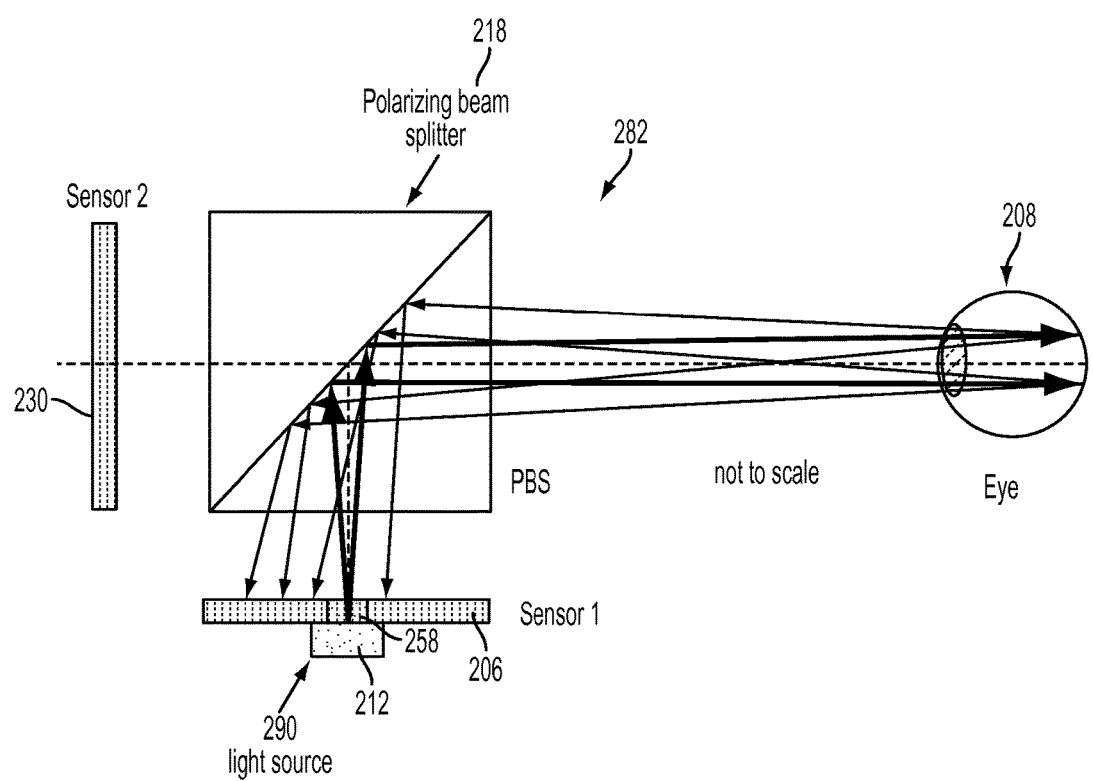
FIG. 13 shows a polarization detecting photodetector using a polarizing beam splitter.

Space permitting, a miniature polarizing beam splitter (PBS) can be used as an alternative to the above described emitter-sensors (FIG. 13). FIG. 13 shows a polarization-sensitive optical transducer 282 including a source 284 of polarized light that has an end portion 258 arranged to project the polarized light; a photodetector 206 that surrounds the source 284 of polarized light and that is in a substantially same plane as the end portion 258 of the source 284 of polarized light, wherein the photodetector 206 senses light from the source 284 of polarized light when the light strikes a polarization-changing object 208 and is back-reflected toward the source 284 and surrounding photodetector 206, wherein the polarization-sensitive optical transducer 282 is configured to detect a polarization state of the back-reflected light, and wherein the polarization-sensitive optical transducer 282 provides information about the polarization changing properties of the polarization-changing object based on the detected polarization state. In one embodiment, the polarization-sensitive optical transducer 282 can include a photodetector 206 that comprises a linear polarizer, as in FIG. 7. In another embodiment, the polarization-sensitive optical transducer 282 can include a source of the polarized light that comprises a pigtail laser diode 128 having a polarization-preserving fiber that extends through a hole in the surrounding photodetector 206. In another embodiment, the surrounding photodetector 206 can include a polarizing beam splitter 218 and two photodetectors 206, 230 arranged for differential polarization measurement of the polarization state of the back-reflected light.

Vertically polarized light coming from a light source (for example, a NIR laser diode) passes through a tiny hole (≤1 mm) in one of the photodetectors, and is fully redirected towards the eye by the polarizing beam splitter 218. The retro-reflected light (for example of elliptical polarization) is decomposed into its two orthogonal components (s- and p-), and the two components are measured by their corresponding sensors simultaneously. The two components are subtracted from each other, thus achieving differential polarization measurement. This embodiment allows measurements without any other optics between the emitter-sensor and the eye, and is applicable to multi-sensor configurations. In contrast to other differential polarization measurement systems, this embodiment can measure returning light of changed polarization without losses that are usually incurred by a non-polarizing beam splitter used to introduce the source of light into the common light path.

Figure 14:
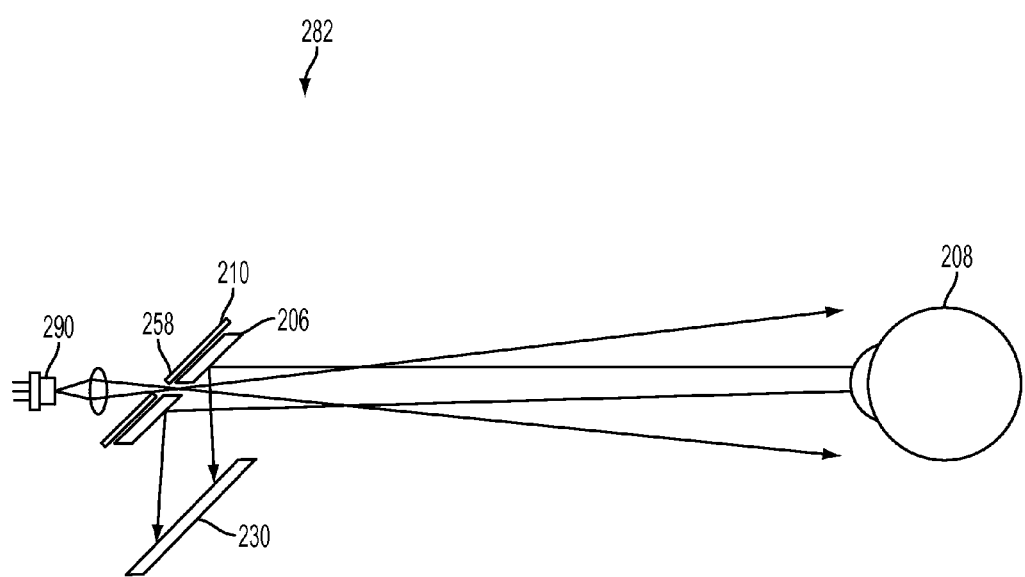
FIG. 14 shows a holed photodetector having a thin film coating that serves as a polarizing beam splitter.

As disclosed in U.S. Pat. No. 4,681,450, the content of which is hereby incorporated by reference in its entirety, a polarimeter can have detectors that are coated with partially reflective coatings, reflecting a portion of the light on to further detectors. In another embodiment, in FIG. 14, a polarization-sensitive optical transducer 282 includes a first-encountered photodetector 286 and a second-encountered photodetector 288 where the back-reflected light is detected by the first-encountered photodetector 286 before the second-encountered photodetector 288, the first-encountered photodetector 286 is tilted in relation to the plane of an end portion 258 of the source of polarized light, and the polarizing beam splitter comprises thin-film layers deposited directly onto a surface of the first-encountered photodetector 286 such that the p-component of the polarized light passes through the thin-film layers and is absorbed by the first-encountered photodetector 286, and the s-component of the polarized light is reflected by the thin-film layers to be absorbed by the second-encountered photodetector 288. While in a previously disclosed embodiment an end portion 258 can be comprised in the part of the source of light or emitter, another embodiment, such as disclosed in FIG. 14, an optical system can include the end portion 258 being part of a light beam that focuses at a particular point. The thin-film layers may be directly deposited on the surface of the holed first-encountered photodetector and may comprise the polarizing beam splitter. P-polarization can pass through the thin-film layers to the holed first-encountered photodetector upon which they are deposited, whereas s-polarization can be reflected by the thin-film layers to be detected by the second-encountered photodetector 288.

Figure 15:
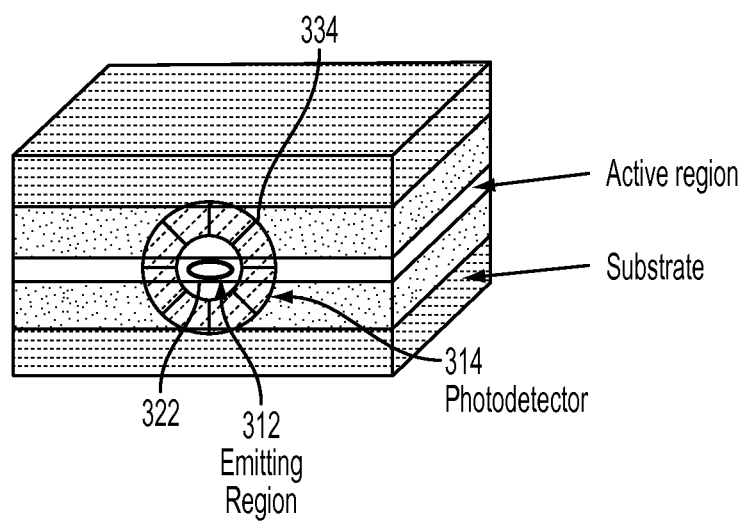
FIG. 15 shows an emitter/receiver as an integrated edge-emitter/photodetector.

As an alternative to the combination of a discrete laser diode and a separate discrete sensor with a hole in the center, as shown in FIGS. 7 and 8, another design of the emitter-receiver is shown in FIG. 15. FIG. 15 shows an element of an eye tracking and gaze fixation detection system 100 where each of the plurality of emitters is an edge-emitting emitter 322. In one embodiment, the edge-emitting emitters 322 can be edge-emitting laser diodes. Here, an edge-emitter laser diode 322 is integrated with a photodetector 314. A custom ceramic sub-mount can be utilized. The photodetector 314 can consist of one or several detectors 334 (here 8). An advantage of the edge-emitter laser diode 332 can include that it can deliver higher power than in other solutions such as the vertical cavity surface emitting laser (VCSEL), presented in the next embodiment.

Figure 16:
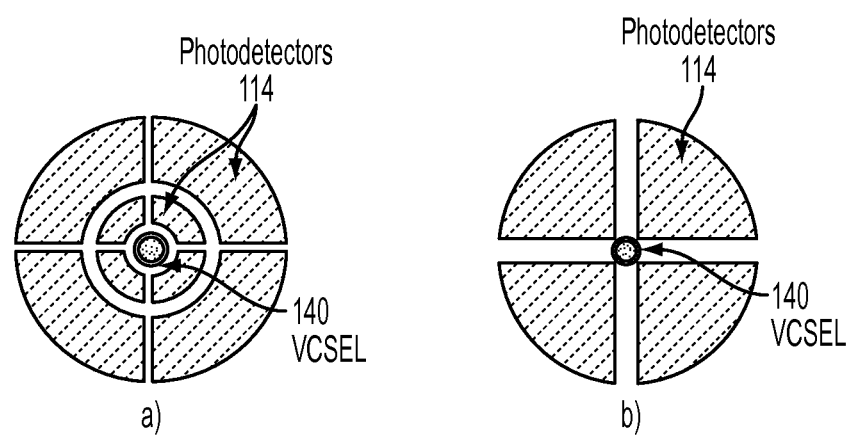
FIG. 16 shows VCSEL-photodetector configurations with the VCSEL in the center of each die.

FIG. 16 shows an eye tracking and gaze fixation detection system 100 where each of the plurality of laser diodes 122 is a vertical cavity surface emitting laser (VCSEL) 140. It is the light source of choice for many optoelectronic applications due to its low threshold, single-longitudinal-mode operation, and low beam divergence. The VC SEL 140 has a more complicated semiconductor structure, but its encapsulation structure is generally simpler. The monolithic integration of VCSELs 140 with photodetectors 114 lends itself to a number of applications because of small size, directionality, high device uniformity, and low optical and electrical crosstalk between devices on the same substrate. FIG. 16 shows two coaxial sensing configurations of the VCSEL 140 surrounded by photodetectors 114. More than one emitter 112 and photodetectors 114 are possible. Thus, in FIG. 16, an eye tracking and gaze fixation detection system 100 can include an optical detection system 104 that comprises a plurality of photodetectors 114 arranged to substantially surround each of the plurality of emitters 112 in a plane substantially common to the location of both the emitters 112 and the photodetectors 114.

Arrangement of Emitter/Photodetectors Around a Small Screen for the Purpose of Eye Tracking.

Figure 17:
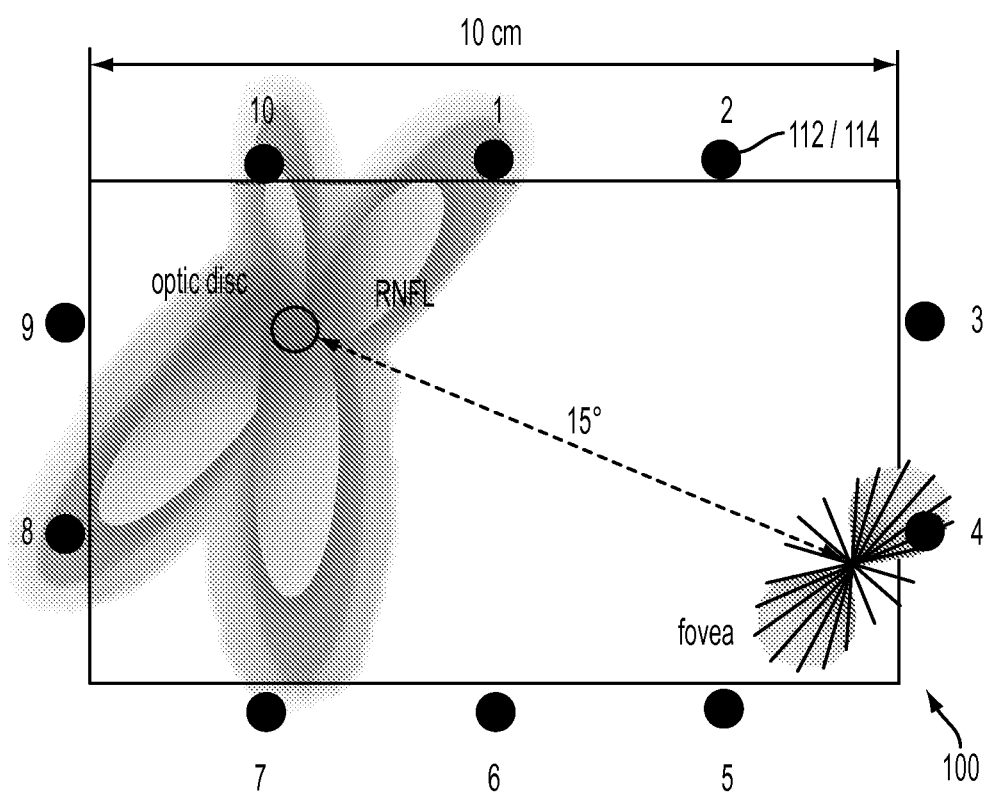
FIG. 17 shows emitter/receivers located around a small-size screen.

FIG. 17 shows how a screen 150 of width approximately 10 cm (~4") would project onto the retina. The foveal projection, identifying the direction of gaze, is shown in the lower right-hand corner, and there is a visual angle of ~15° between the fovea and the optic disc (the center of the thickest portion of the retinal nerve fiber layer (RNFL)). Ten emitter/sensors are positioned in the periphery of the screen 150. In this example, birefringence signals of different intensity would be measured in photodetectors 1, 4, 7, 8 and 10. Different photodetectors may be affected by light coming from the other eye, and some sensors will capture retro-reflections coming from both eyes. After calibration, the intensities measured in each photodetector allow proper identification of the direction of gaze. Thus, FIG. 17 shows an eye tracking and gaze fixation detection system 100 where the plurality of emitters 112 and the plurality of photodetectors 114 are positioned outside a periphery of a screen 150 that is adapted for the subject to gaze at.

Processing of the Information Obtained from the Sensors.

In one embodiment, one of the emitters emits, while all photodetectors receive. With n emitter-photodetectors of which only one emits at a time, the retro-reflected intensities of NIR light received can be presented as a measurement matrix S:

$$S = \begin{bmatrix} S_{11} & \cdots & S_{1n} \\ \vdots & \ddots & \vdots \\ S_{n1} & \cdots & S_{nn} \end{bmatrix} \quad (3)$$

where $S_{ij}$ is the signal measured on photodetector i when emitter j is on. The problem is reduced to finding the coordinates of the point of fixation (x,y) (see FIGS. 1 and 2) when all elements $S_{ij}$ of matrix S during incoming measurements in real time are known. To achieve this, generally calibration information is needed. During calibration, the user is asked to fixate on different fixation points on the screen, and each time a matrix $S^q$ is acquired. The results of the calibration are then stored in a tensor $S^{nnp}$ of size n×n×p where p is the number of calibration measurements (1 . . . q . . . p).

One realization of one embodiment is to calculate a transformation matrix A of dimension n×2 such, that when applied to the incoming matrix S of dimension n×n, the coordinates x and y of the eye gaze will be estimated:

$$[x,y] = S \times A \quad (4)$$

The calculation of the transformation matrix A involves methods from linear algebra. This method can have an advantage that all calibration information is used in a straightforward manner.

Figure 18:
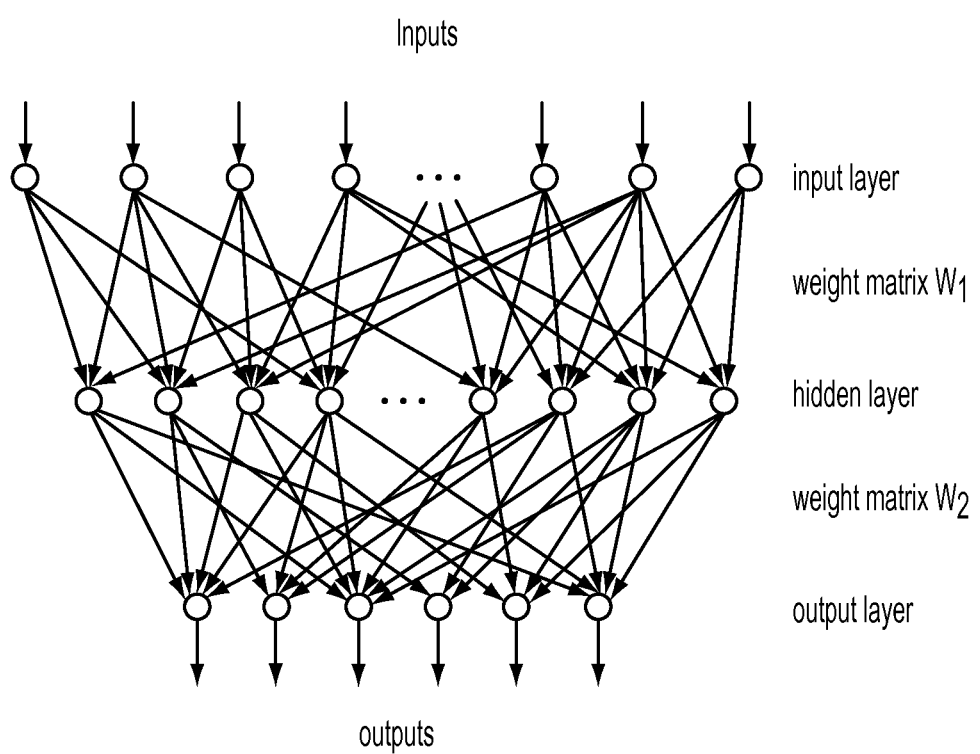
FIG. 18 shows the general neural networks architecture used for eye tracking.

An alternative realization involves a classical feedforward neural net algorithm of the type shown in FIG. 18. The number of the inputs in the general case is n×n (the size of the photodetector matrix S). For faster, less computationally intensive algorithms, subsets of S may be used. In the simplest case, only the diagonal elements $S_{ii}$ of S are used, i.e. each time an emitter is fired, only its own sensor is measured and used for computation. The hidden layer nodes (neurons) operate using a weight matrix and sigma type of function. The neural net may be implemented as binary, i.e. a cutoff threshold function is appended to the sigma function of each node in the hidden-layer and output layer. In this case, each output is a class, and only one class can be active. In terms of eye tracking, this means that the eye is fixating on a point within a certain area of the visual field. The number of areas of interest (classes) is the number of the (digital) outputs of the net. The larger the classes, the faster is the calibration and the training of the net. Alternatively, a perceptron type of analog neural network uses an analog activation function (instead of binary threshold function) at each node, and calculates the coordinates of fixation x and y in analog form. In this case the neural net will only have two analog outputs. The precision with which fixation x and y are estimated depends on the number of inputs (sensors used each time), the training set, and the number of hidden layers.

These instruments in one embodiment use only retinal information with no-moving-part fixation monitors. U.S. Pat. No. 6,027,216, the content of which is hereby incorporated by reference in its entirety, discloses a method and devices that use the birefringence of the nerve fibers surrounding the human fovea (Henle fibers) and their strict radial geometry (FIG. 4) to monitor foveal fixation and to detect proper alignment of the two eyes in infants and young children for the purpose of vision screening and early detection of strabismus with attendant amblyopia. Using the eye in an auto-conjugate arrangement, these first instruments employed a motor-driven circular scanning system, as disclosed in U.S. Pat. No. 8,678,592, the content of which is hereby incorporated by reference in its entirety. When the eye was focused on the intended fixation point (a light source in the center of the circular scan), the light reflected from the retinal scan would be automatically focused by the eye back to the source, where it could be deflected by a beam splitter and measured for changes in polarization state induced by double passage through the Henle fibers. With central fixation, because the scanning path was a circle centered around the center of the foveal bow-tie, the polarization state of the light changed at twice the frequency of the scan, 2f. With paracentral fixation, however, the change in the polarization state was only at the frequency of the scan f.

The rapidly spinning motor, however, added noise and vibration, and was generally of limited life. To avoid these problems, an embodiment of the current invention can provide a no-moving-parts eye fixation monitor. Instead of circular scanning, this class of instruments utilizes several sources/spots (n≥5) of linearly polarized light can be arranged in a closed loop to obtain spatial information about the position and intensity of the bow-tie. In one embodiment, the closed loop is a circle of ~3° visual angle with respect to the eye. An embodiment that uses a closed loop can be directed to a raster scan that performs x-y scanning.

Figure 19:
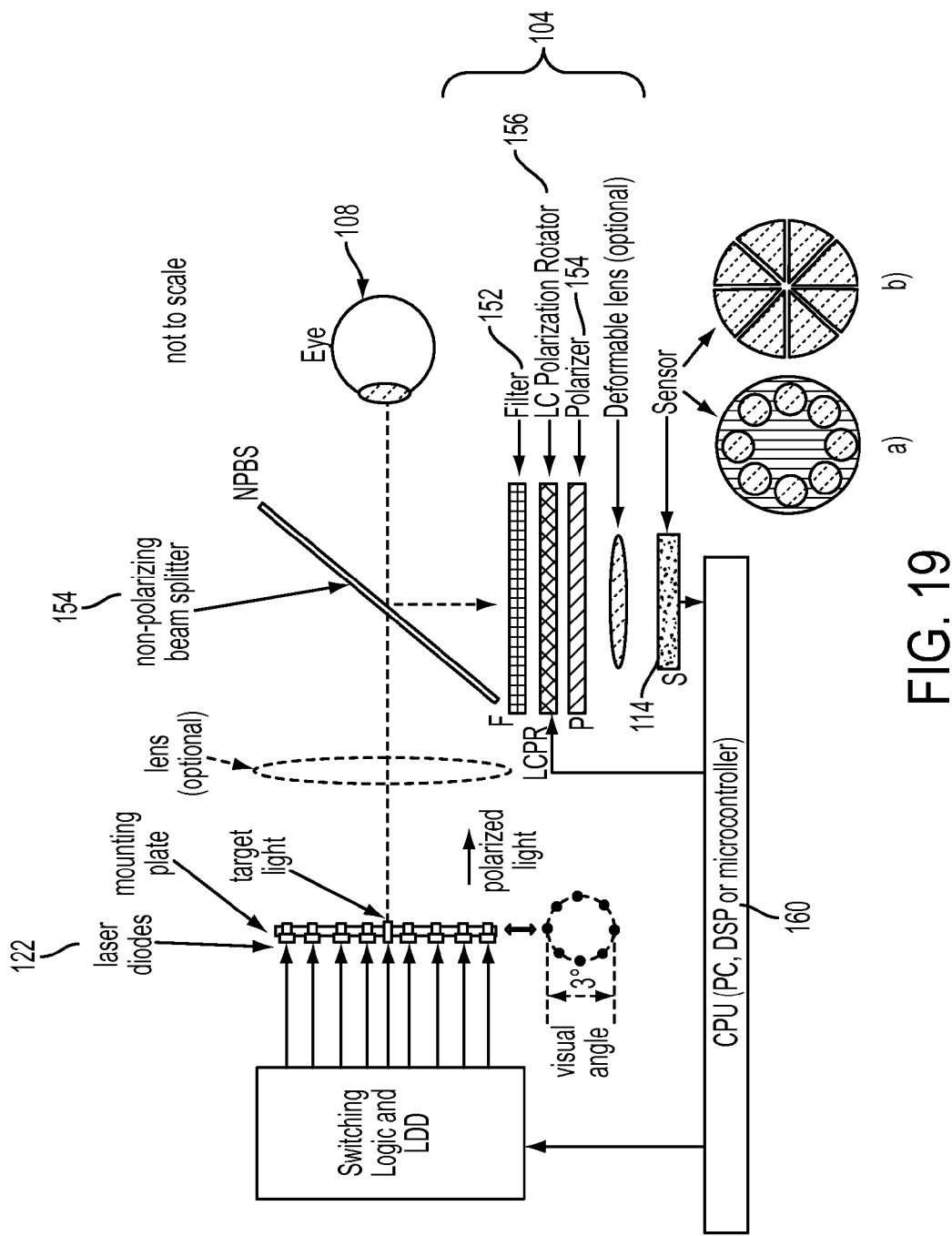
FIG. 19 shows an eye tracking and fixation detection system using laser diodes with two possible photodetector configurations.

FIG. 19 shows an eye tracking and gaze fixation detection system 100 including an interference filter 152 arranged in the optical path of the NIR light from the electronically scannable optical illumination system 102 after being reflected from the eye 108 of the subject prior to being detected by the optical detection system 104. In FIG. 19, the light reflected from the fundus and diverted by the beam splitter travels through an interference filter 152 tuned to the wavelength of the laser diodes 122, a liquid crystal polarization rotator (LCPR) 156, typically a twisted nematic (TN) device, a polarizer 154, and onto the photodetector 114. The interference filter 152 can be an optical band-pass filter in one embodiment. Two measurements can be taken—one at a first rotation of the returning polarization states, and one with the LCPR 156 rotating the polarization states of the light by 90° with respect to said first rotation. This can achieve two goals: a) the full $S_1$ component of the Stokes vector (s-p) can be measured, and b) depolarized back-reflections from the skin of the face can be eliminated.

FIG. 19 shows an example of a no-moving-parts fixation monitor that is an eye tracking and gaze fixation detection system 100. The laser diodes 122 can be fired one at a time, or in groups of spatially separated laser diodes 122, in succession by the CPU 160 and the switching logic, thus interrogating spots on the retina, presumably around the fovea. The light retro-reflected by the fundus is diverted by the non-polarizing beam splitter 154 toward the photodetector 114. The photodetector 114 has n active parts, each one being optically conjugate to one of the laser diodes 122, and is expected to receive light from a corresponding spot on the retina.

Alternative designs also have an array of individual emitters. These can include multiple images of a single emitter, achieved by prismatic, mirror, holographic, or other image multiplying means such as a single, fiber-coupled, polarization-maintaining laser diode with a computer-controlled optical switch routing the output of the single laser diode to the array of discrete emitter sites, as shown in FIG. 12. These alternative approaches can have the advantage of equal intensity from each of the multiple emitter sites. Likewise, an image combining technique in the reverse direction may allow the use of a single detector.

Figure 20:
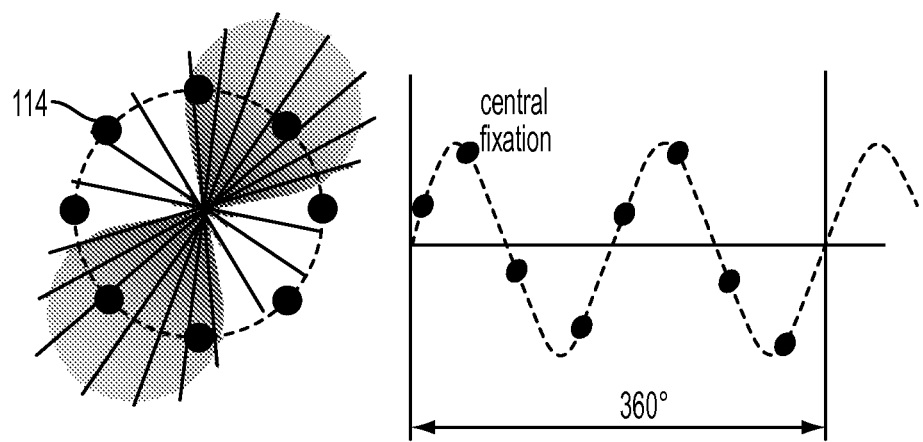
FIG. 20 shows the interrogation of the retina during central fixation around the fovea and the corresponding frequency of the interrogation results.
Figure 21:
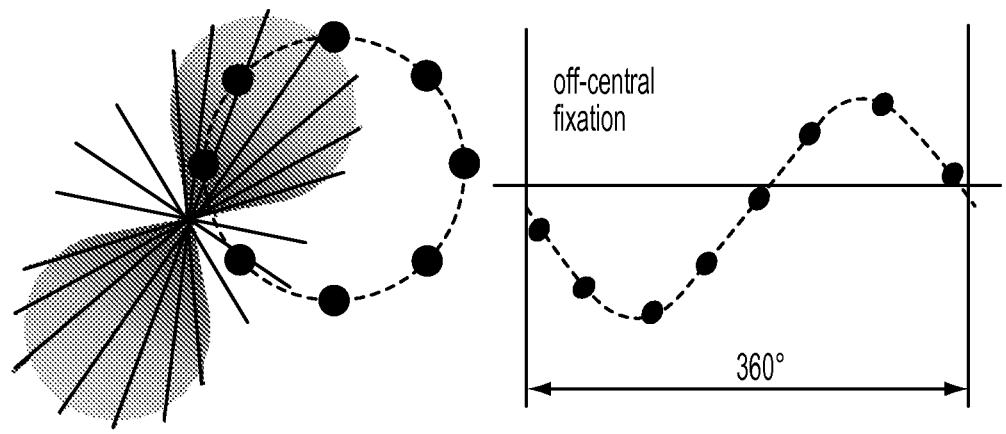
FIG. 21 shows the interrogation of the retina during off-central fixation in the vicinity of the fovea and the corresponding frequency of the interrogation results.

With central fixation, as seen in FIG. 20, the center of the circle coincides with the center of the bow-tie of polarization states, and with a sufficient number of photodetectors 114 (n≥5) the doubling of the frequency may be identified using Fourier analysis. With off-central fixation, as seen in FIG. 21, the interrogating circle does not encompass the center of the fovea, and the interrogating signal does not yield a frequency doubling.

Figure 22:
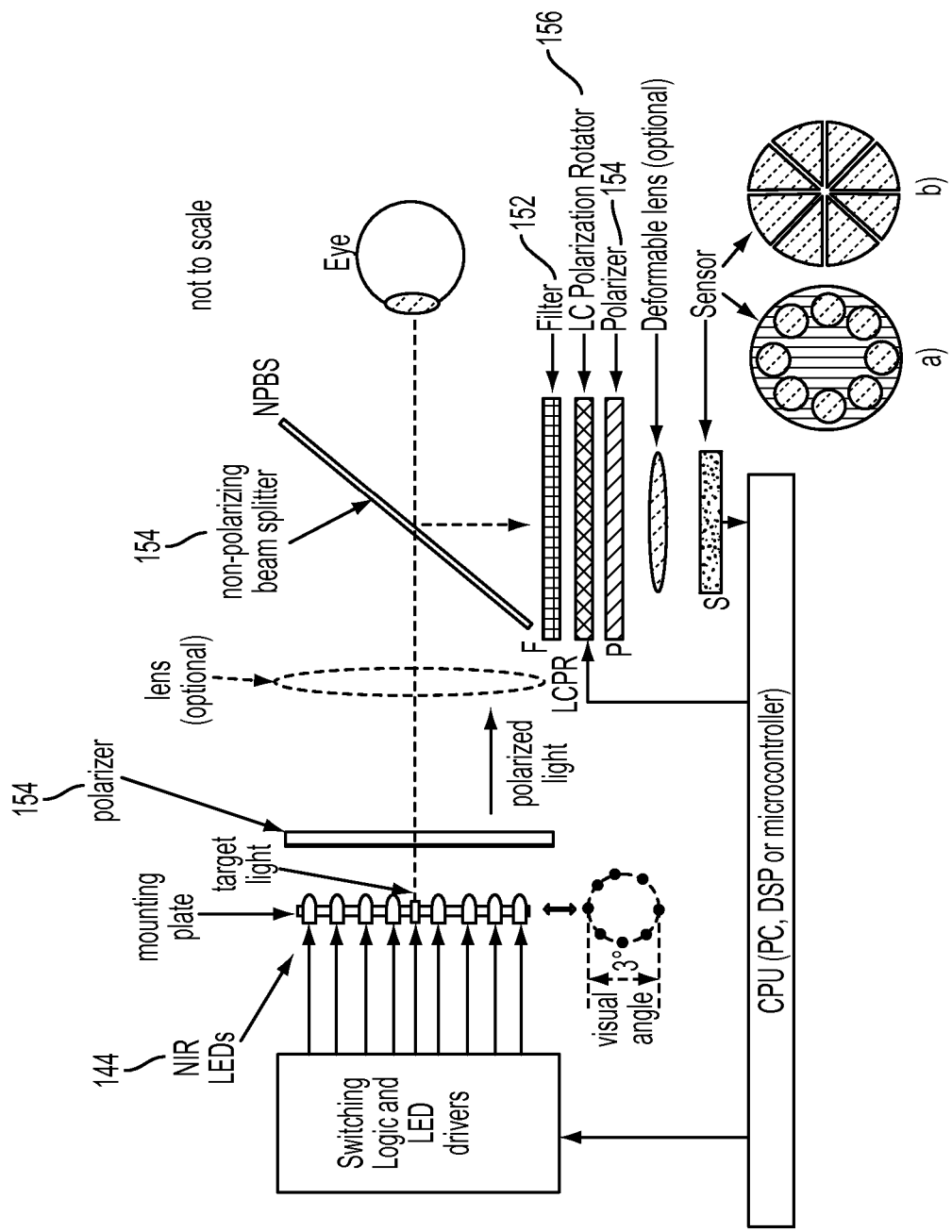
FIG. 22 shows an eye tracking and fixation detection system using NIR LEDs.

A modified embodiment is presented in FIG. 22, which shows NIR light-emitting diodes (LEDs) 144 along with a polarizer 154 instead of laser diodes. In one embodiment, as shown in FIG. 22, an eye tracking and gaze fixation detection system 100 includes each of the plurality of emitters 112 comprising a light-emitting diode 122, and the electronically scannable optical illumination system 102 comprising a polarizer 154 disposed in an optical path between the emitters 112 and the subject.

Figure 23:
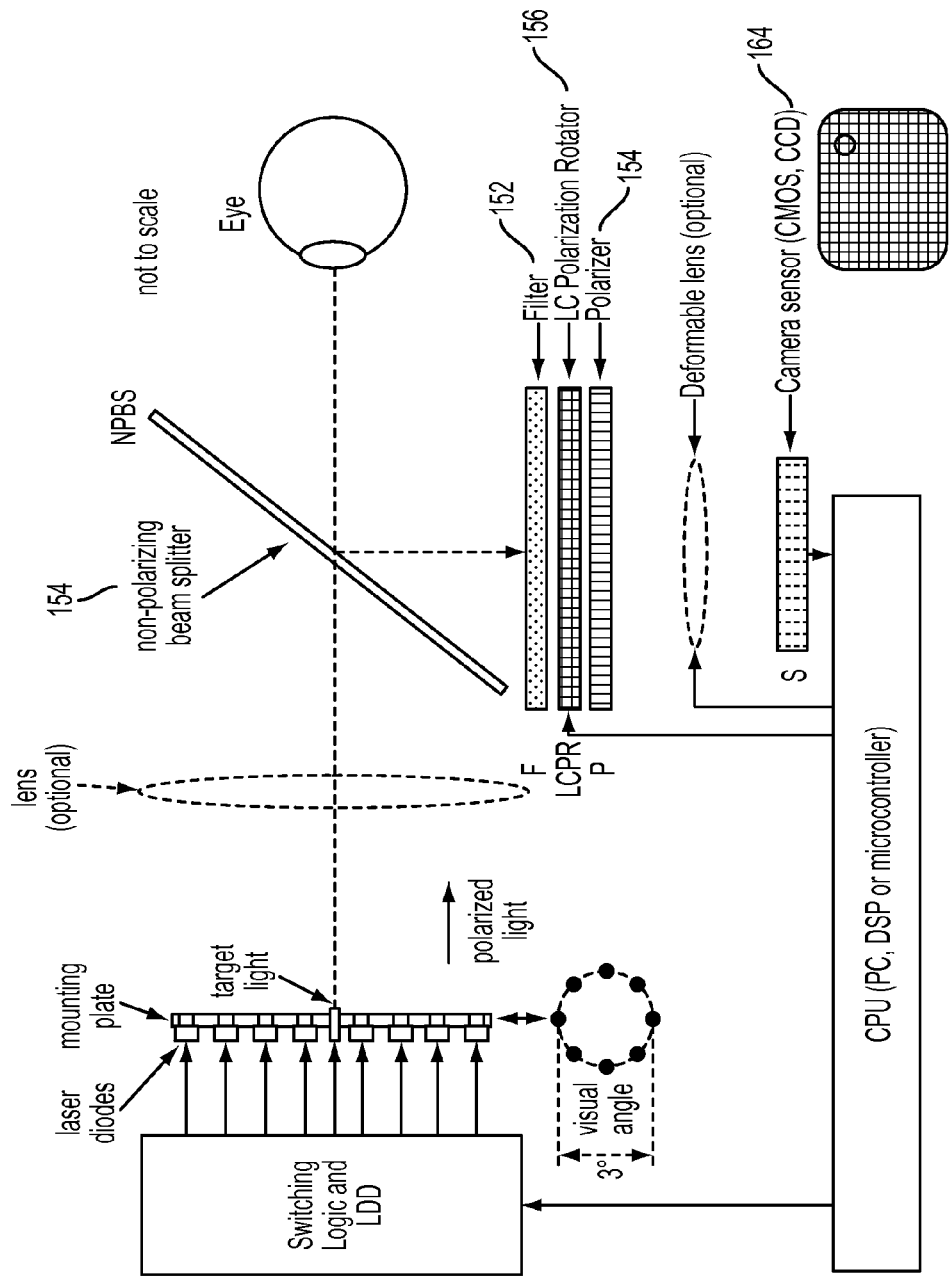
FIG. 23 shows an eye tracking and fixation detection system using laser diodes and a sensing array.
Figure 24:
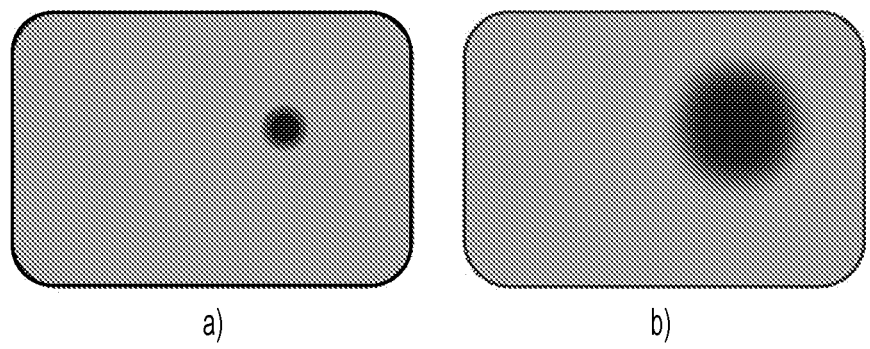
FIG. 24 shows estimating the level of defocus by the size of the spot registered on a sensor array.

In FIG. 23, laser diodes 122 are used as sources of polarized light, but the photodetector 114 (typically a multi-segmented photodetector) is replaced by a high efficiency photon sensing array (camera chip or camera sensor) of CCD or CMOS type. Thus, FIG. 23 shows an eye tracking and gaze fixation detection system where the plurality of detectors comprises an image sensor array. The sensor can be a multi-segmented photodetector, or a high efficiency photon sensing array (camera chip) of CCD or CMOS type, as shown in the previous embodiments. Using an array can have several advantages:

a) using image processing methods, parasitic reflections from the face can be fully eliminated,
b) the differential polarization detection method allows for efficient removal of image components not caused by the birefringence of the Henle fibers,
c) an electronically controlled deformable lens can be included, to help find the optimal focus,
d) judging by the spot registered each time a laser is flashed, the focus/defocus of the system can be estimated, along with the presence or absence of central fixation (FIG. 24), and
e) after calibration, eye-tracking can be implemented, based on the information obtained from the n spots on the retina.

Figure 25:
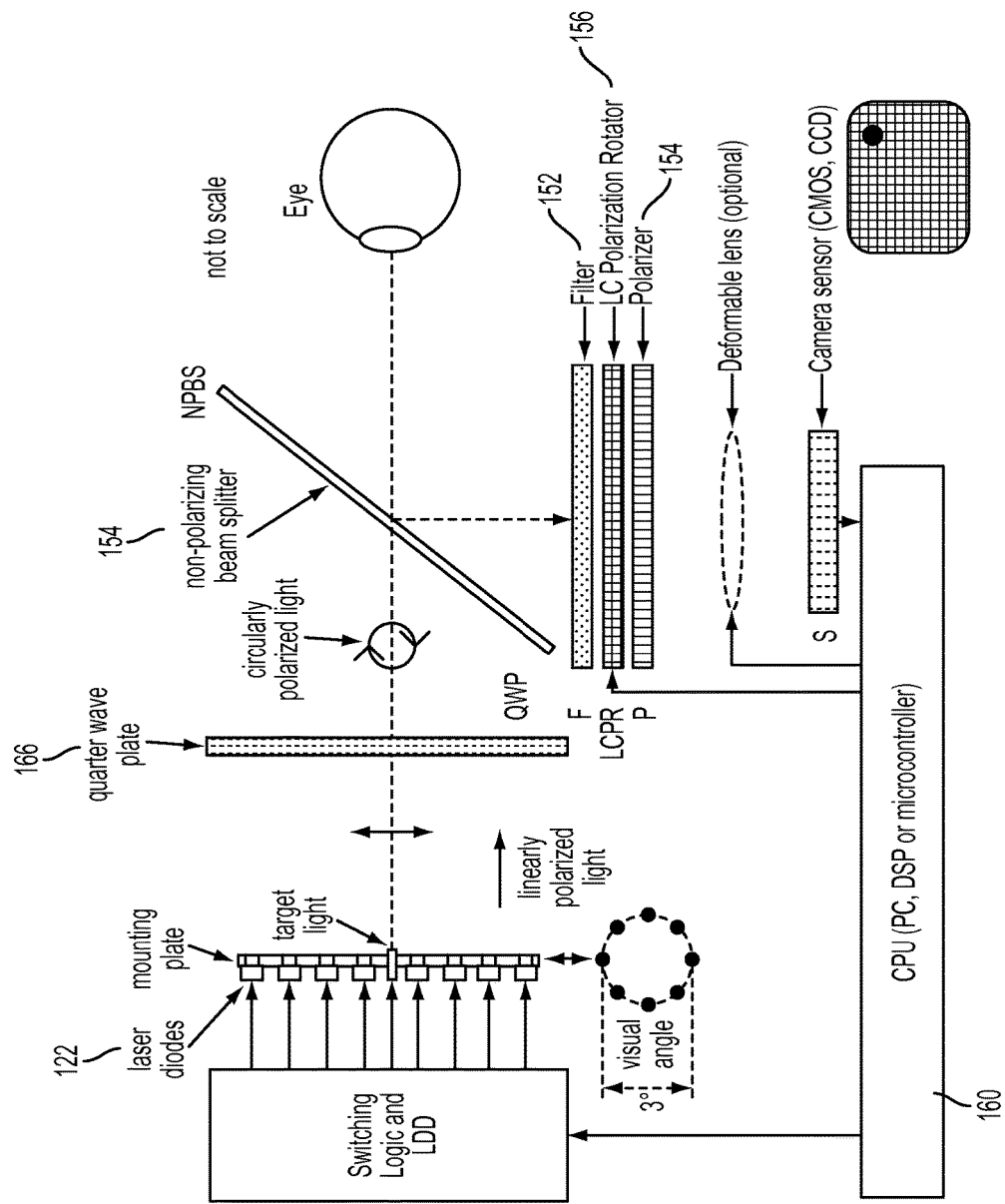
FIG. 25 shows an eye tracking and fixation detection system using laser diodes and a quarter wave plate.

Another embodiment is shown in FIG. 25. This embodiment uses laser diodes 122 as sources of (linearly) polarized light, and a quarter wave plate (QWP), sending circularly polarized light into the eye. This design reduces interference caused by specular reflections, and variability among eyes caused by differences in corneal birefringence. Differential polarization detection in this case is achieved by means of a LCPR 156, rotating the elliptically polarized light returning from the retina by 90°, and an analyzing polarizer 154.

Compensation of Corneal Birefringence.

Figure 26:
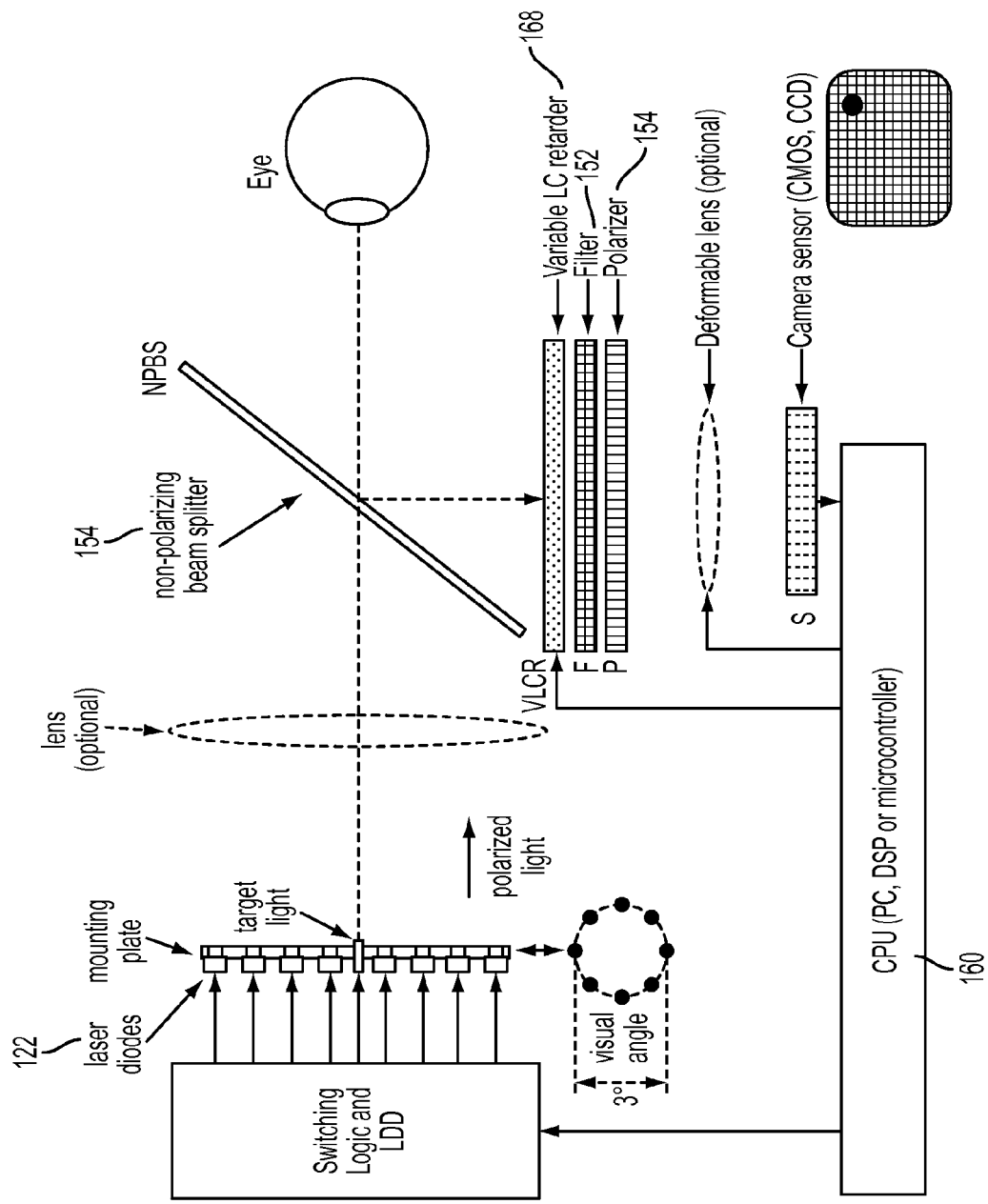
FIG. 26 shows an eye tracking and fixation detection system using an electronically controlled variable liquid crystal retarder.

Corneal birefringence, being several times higher than that of the retina, is known to adversely affect the measurement of the retinal birefringence. There are significant variations in corneal retardance and azimuth across the population. This means that the measured signal in two individuals can be very different due to differences in the corneal birefringence alone. This can be solved by introducing an individual compensation of the corneal birefringence by means of a variable liquid crystal retarder (VLCR) in the measurement path, controlled by the CPU, as shown in FIG. 26. FIG. 26 shows an eye tracking and gaze fixation detection system 100 including a variable liquid crystal retarder 168 arranged in the optical path of the NIR light from the electronically scannable optical illumination system 102 after being reflected from the object of interest prior to being detected by the optical detection system 104. Before the actual measurement, with the test subject fixating at a target, the system 100 keeps taking measurements while changing the retardance—first in larger steps, then in smaller, until the amplitude is maximized.

Rotating the Orientation of Polarization.

Figure 27:
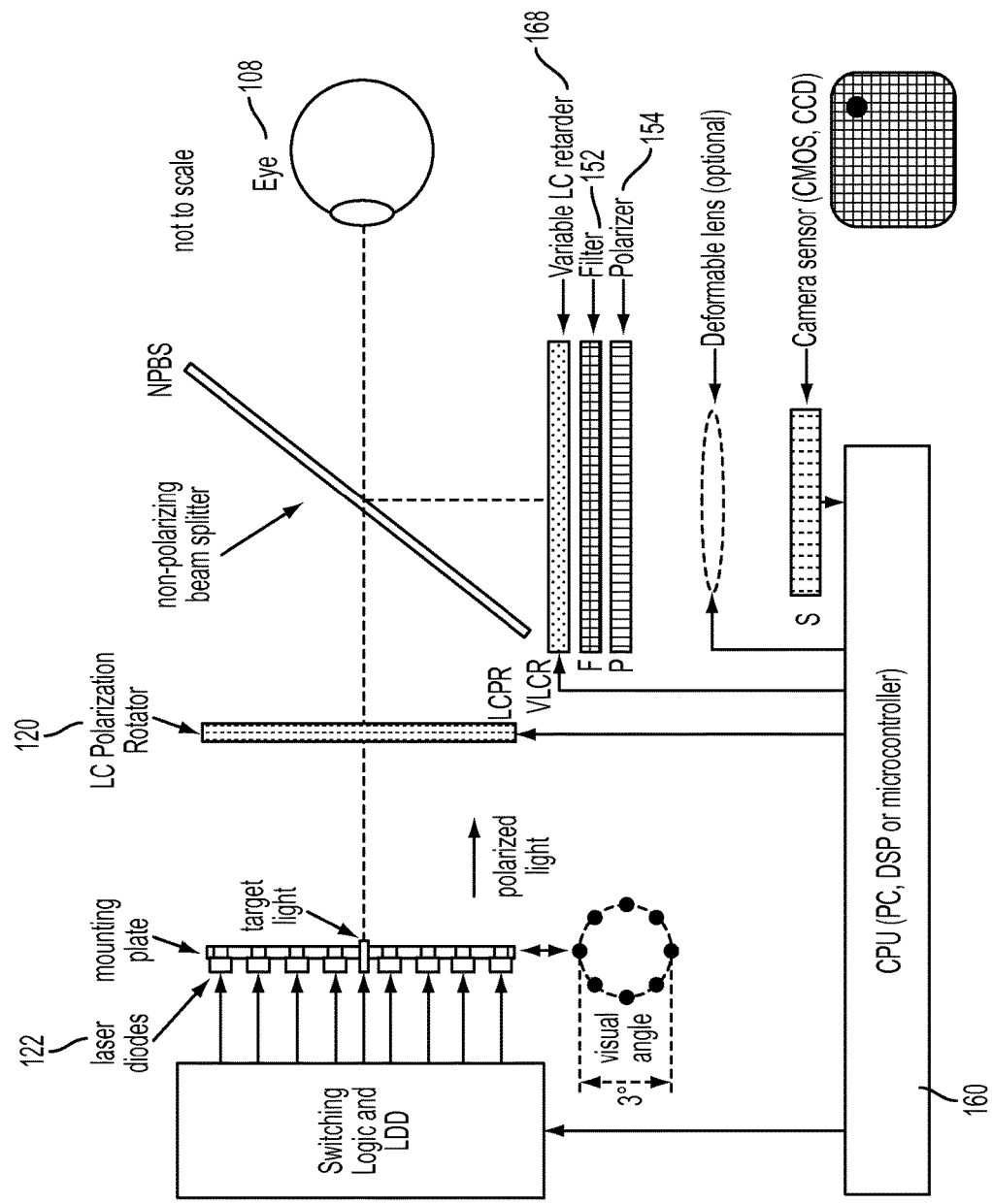
FIG. 27 shows an eye tracking and fixation detection system using a liquid crystal polarization rotator.

Previous designs with circular scanning systems have shown that when the orientation of incoming polarization is rotated at a rate $x^*f_{scan}$, ($x \ne 1$ or 0), the signal at the sensor contains specific frequencies, characteristic of central fixation, and other frequencies, specific of para-central fixation, and other frequencies substantially independent of the fixation or non-fixation state of the subject's eye. These frequencies depend on x, and can be detected with a sufficient number of light sources and corresponding optically conjugate sensors, or a with a camera sensor. In FIG. 27, the eye tracking and gaze detection system 100 includes an electronically scannable optical illumination system 102 that includes a liquid crystal polarization rotator (LCPR) 120 arranged to rotate the plane of polarization of the light from the laser diodes 122 to enhance the detection signals. FIG. 27 shows a realization of this method, where the incoming polarization is rotated by means of the LCPR 120 under CPU control during data acquisition, being adjusted for every laser diode 122 before acquiring data from the area on the sensor that matches it. The laser diodes 122 are activated at a speed $f_{scan}$ whereas the polarization is spun at a speed $x^*f_{scan}$. Spectral analysis involving the output at n interrogating points then reveals the characteristic frequencies. Maximization of the signals through individual compensation of the corneal birefringences is achieved by means of a variable liquid crystal retarder (VLCR) 168 in the measurement path, also controlled by the CPU, as shown in a previous design.

Figure 28:
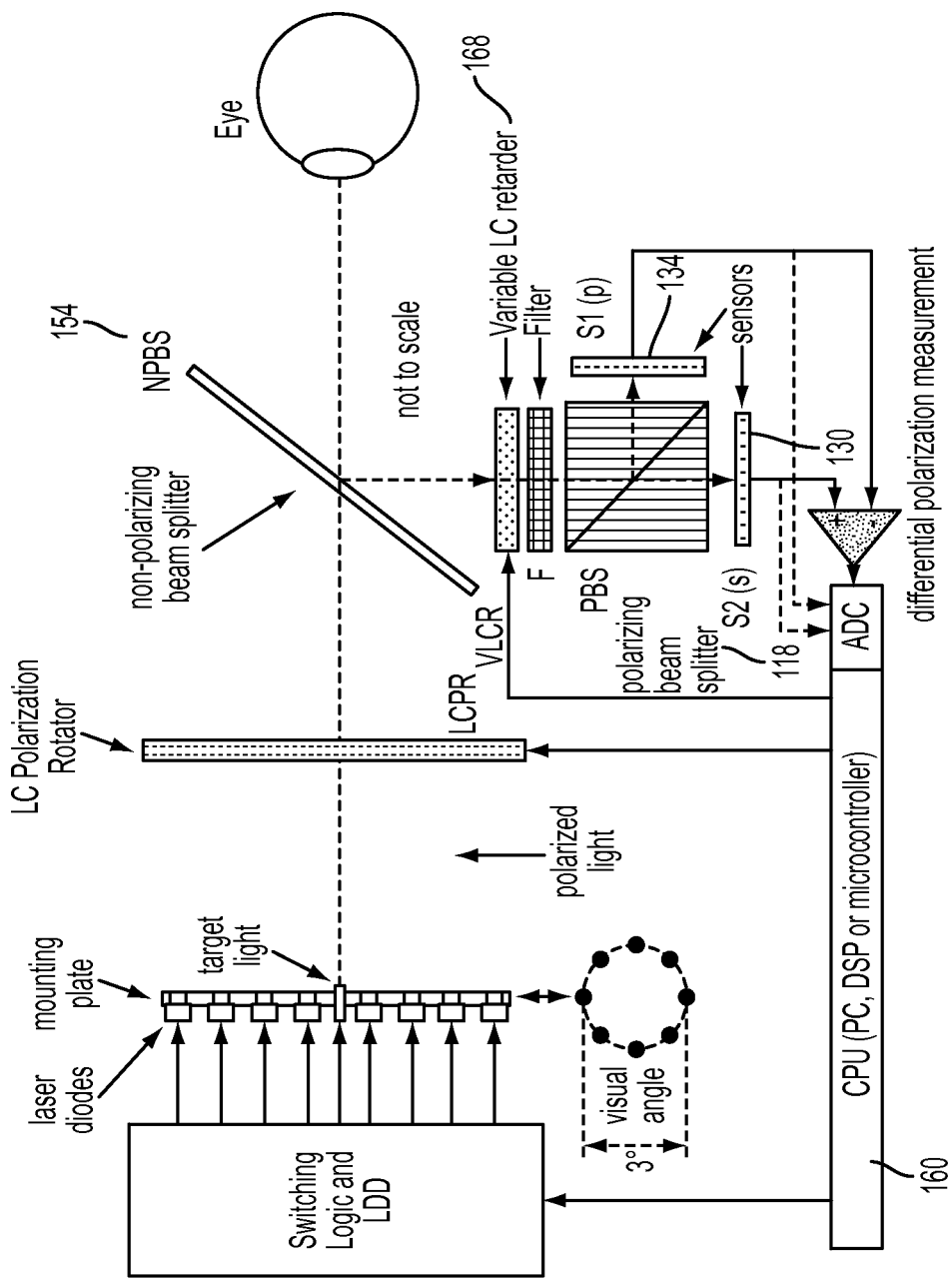
FIG. 28 shows an eye tracking and fixation detection system using a polarizing beam splitter.

Another embodiment is shown in FIG. 28, which uses laser diodes 122 as sources of (linearly) polarized light, and a computer-controlled liquid crystal polarization rotator (LCPR) 116, sending linearly polarized light of constantly changing orientation of the polarization plane into the eye 108. Differential polarization detection in this case is achieved by means of a polarizing beam splitter (PBS) 118 and two sensors 130, 134 measuring simultaneously the p- and the s-component respectively. The difference of the two components can be built in hardware, or in software. This design has an advantage over the previous one (which uses a polarizer instead of the PBS) in that it measures the full $S_1$ component of the Stokes vector. The sensors 130, 134 can be two multi-segmented photodetectors, or two high efficiency photon sensing arrays of CCD or CMOS type, as shown in the previous embodiments. Maximization of the signals through compensation of the individual corneal birefringence is achieved by means of a VLCR 168 in the measurement path, controlled by the CPU, as shown in a previous design.

Figure 29:
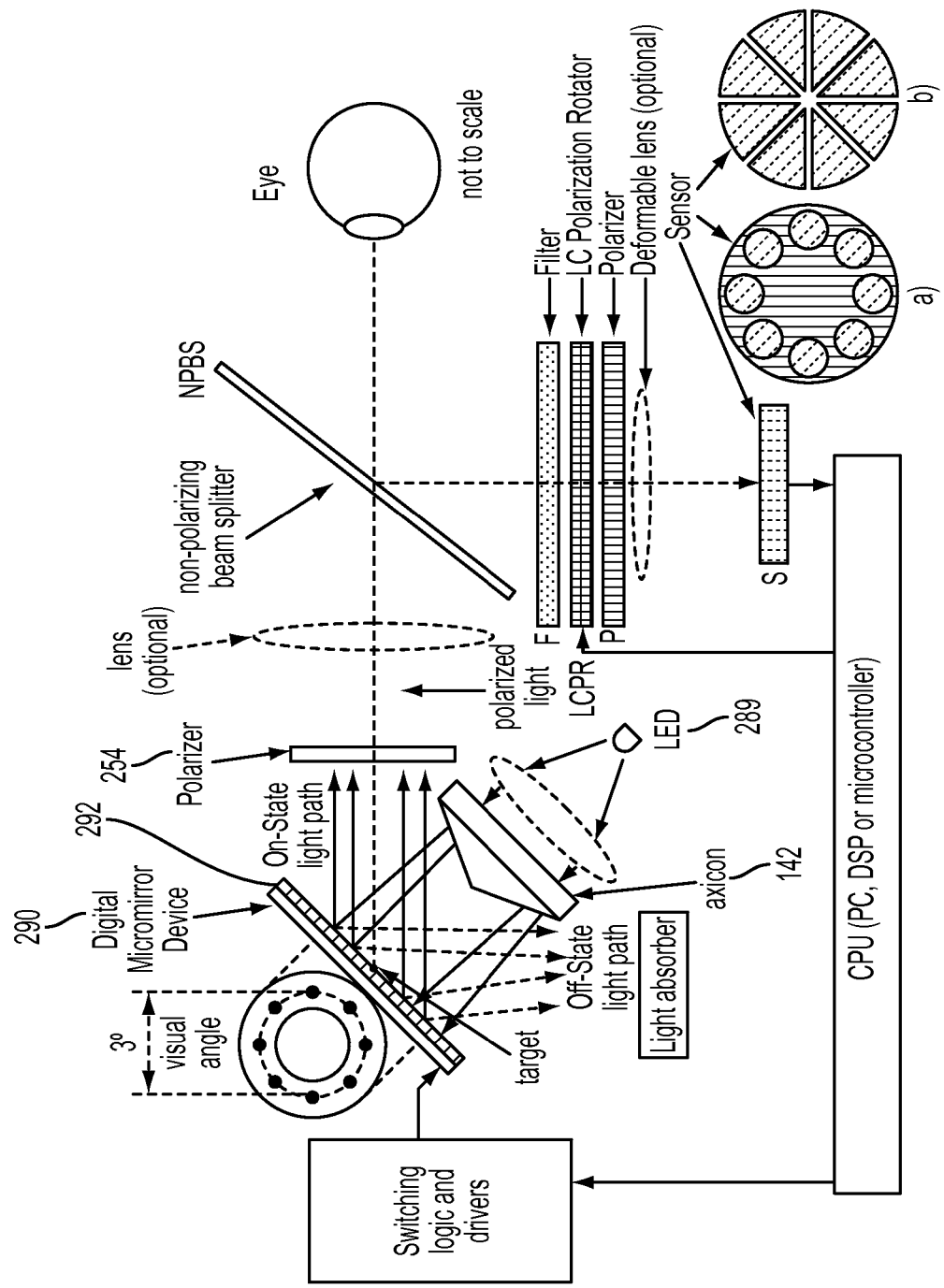
FIG. 29 shows an eye tracking and fixation detection system using a digital micromirror device.

FIG. 29 shows an eye tracking and gaze fixation detection system 200 where the electronically scannable optical illumination system 202 comprises a digital micromirror device (DMD) 290 comprising a plurality of micromirrors 292 and a source 284 of NIR light arranged to illuminate at least a portion of the DMD 290 and where the plurality of micromirrors 292 are configured to have electronically addressable ON and OFF states to provide a timed sequence of NIR light corresponding to at least a portion of the scanning path. Thus, the scanning sources of light (e.g., laser diodes, LEDs etc) in other embodiments can be replaced here with the DMD 290 which can produce different patterns capable of reflecting light towards the eye. The patterns can be produced by the CPU 260 with the help of control logic, which can be a standard DLP (Digital Light Projector) board. Mirrors in the active (ON) state redirect light from the NIR source 284 (LED or laser diode) toward the eye, while mirrors in the passive (OFF) state send light away from the eye and the rest of the optics, into a light absorber. Any pattern can be generated. In this example, eight spots of light are turned on and off in succession, thus creating a scanning light "running" in a circle, as in the previous designs. Each bright spot on the DMD 290 illuminates a certain spot on the retina, the reflected light from which is captured by a corresponding segment of the sensor. To increase efficiency, the light from the main source is passed through an axicon 142, which concentrates it in a circular band encompassing the areas on the DMD 290 to be activated. The axicon 142 in this embodiment can serve a similar purpose as the axicon 142 of an embodiment of FIG. 30.

Figure 30:
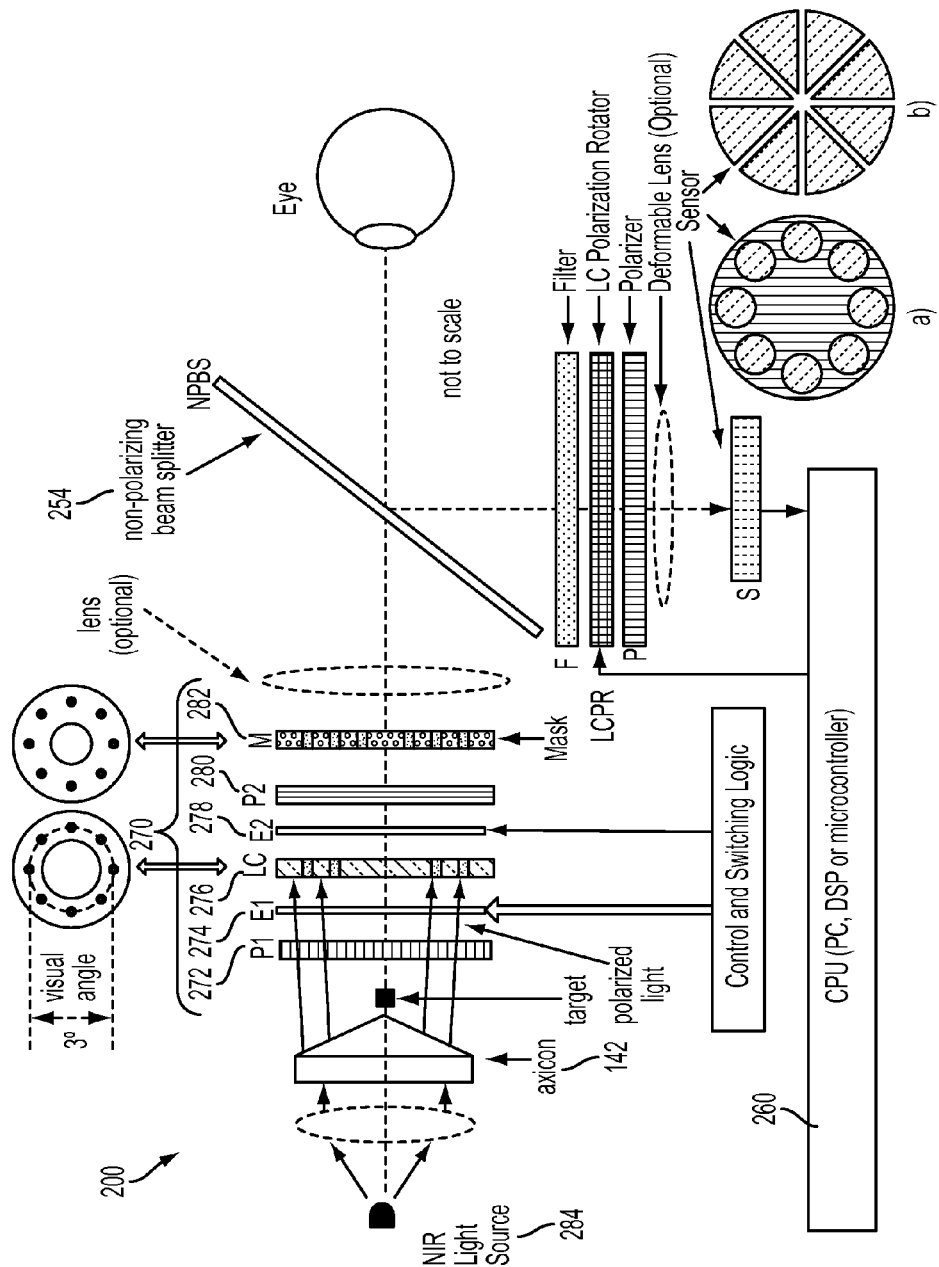
FIG. 30 shows an eye tracking and fixation detection system using a liquid crystal shutter.

FIG. 30 shows an eye tracking and gaze fixation detection system 200 where the timed sequence of the plurality of emitters 212 is determined by electronically addressable liquid crystal (LC) shutters 270 arrayed before the emitters 212 that allow emission of the NIR light of the emitter through the electronically addressable liquid crystal shutters 270 in the sequence. In this design, patterns of lights are produced by turning different spots on a LC shutter 270 ON and OFF. In this embodiment, a passive matrix is used. The LC shutter 270 comprises (left-to right): a first polarizer (P1) 272, a transparent electrode pattern (E1) 274 (consisting of several individually addressable spots), a liquid crystal (LC) 276, a common transparent electrode (E2) 278, and a second polarizer (P2) 280, which is in cross-polarizing orientation with respect to the first polarizer 272. The light spots are generated by applying appropriate voltage to the spots on transparent electrode pattern 274 that need to become transparent in the LC 276 underneath. Before applying an electric field, the orientation of the LC 276 molecules is determined by the alignment at the electrode surfaces. In the case of a twisted nematic device (the most common LC device), the surface alignment directions at the two electrodes are perpendicular to each other, and so the molecules arrange themselves in a helical structure (twist). The double refraction (birefringence) of the crystal causes a rotation (ideally close to 90°) of the linear polarization of the light passing though; therefore most of it is transmitted through the second polarizer. Consequently, the particular spot appears transparent-to-slightly-grey after the second polarizer. When voltage is applied to transparent electrode pattern 274 for the same particular spot, the long molecular axes of the LC 276 between this transparent electrode pattern 274 and the common-plane electrode tend to align parallel to the electric field, thus gradually untwisting in the middle of the LC 276 layer. The orientation of the polarized light is no longer rotated and the light is blocked by the second polarizer 280 from passing through. A mask (M) 282 placed after the second polarizer 280 allows light only from the spots of the pattern to be passed towards the eye. The LC 276 can also be operated between parallel polarizers, in which case the bright and dark states are reversed: the voltage-off dark state blocks the light, and light is passed only through areas under active (voltage-on) electrodes transparent electrode pattern 274. In this case, the device may be operated without the mask 282. Further, if the light source provides polarized light (as is the case with a laser diode), then there would be no need of the first polarizer 272. Further, FIG. 30 shows that an eye tracking and gaze fixation detection system 200 includes an electronically scannable optical illumination system 202 comprising an emitter 284 of NIR light that is arranged to continuously emit NIR light in a timed sequence, and the timed sequence of emission of the source being determined by electronically addressable liquid crystal shutters 270 arrayed before the source that allows emission of the NIR light through the electronically addressable liquid crystal shutters 270 in the sequence.

Spots are activated in succession, thus creating a scanning light "running" in a circle, as in the previous designs. Each bright spot produced by the shutter illuminates a certain spot on the retina, the reflected light from which is captured by a corresponding segment of the sensor. A spot on the liquid crystal can be made opaque or transparent to create one spot at a time and to create a running spot. Mini-sectors of the sensor can be individually applied without adjacent sectors interfering with each other. Two or more emitters can be activated at a time if they are far enough apart from one another that the returning somewhat blurred light from the fundus originating from each emitter cannot reach the detector(s) associated with the other emitter(s). To increase efficiency, the light from the main source is passed through an axicon 142, which concentrates it in a circular band encompassing the areas on the LC 276 to be activated.

FIG. 31 shows a design that includes an array 194 of combined emitter 112-photodetectors 114, onto which the fovea is projected. Since the signal is the change of polarization, the array is capable of scanning the whole bow-tie shape, one emitter-detector at a time. If observed from about 40 cm distance, in order to cover the fovea, this array will need to be a square of ca. 1"×1", i.e. each emitter-detector will be 6 mm×6 mm in the case of a 4×4 array. The lasers can be of either VCSEL or edge emitter type, and can be individually addressable, to be turned on one at a time. All photodetectors 114 are accessible simultaneously, although of greatest interest is to read the photodetector 114 corresponding to its own laser, because the eye lens is expected to reflect and focus the received light onto the same emitting spot, slightly blurred. The position of the bow-tie with respect to the center of fixation (center of the array) can be derived using software pattern identification.

Figure 32:
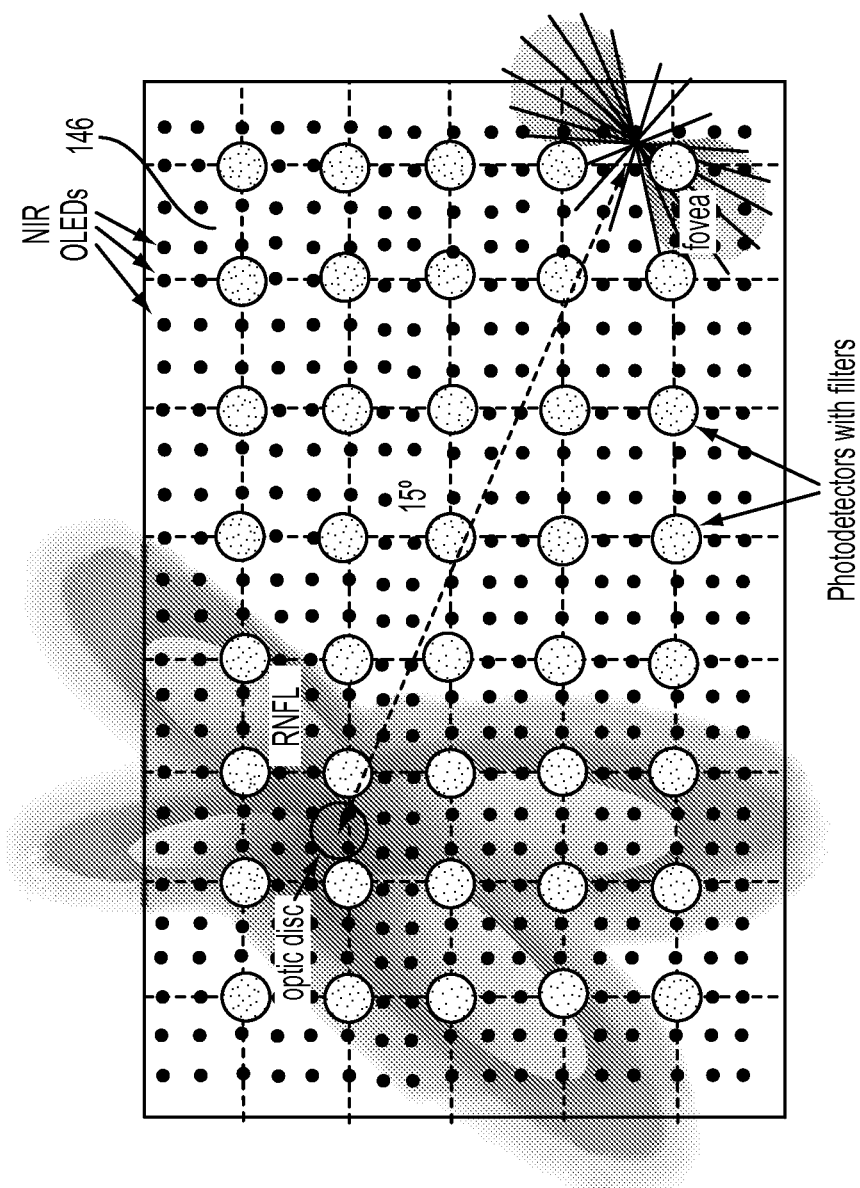
FIG. 32 shows emitters-detectors integrated on an OLED-on-CMOS microdisplay.
Figure 33:
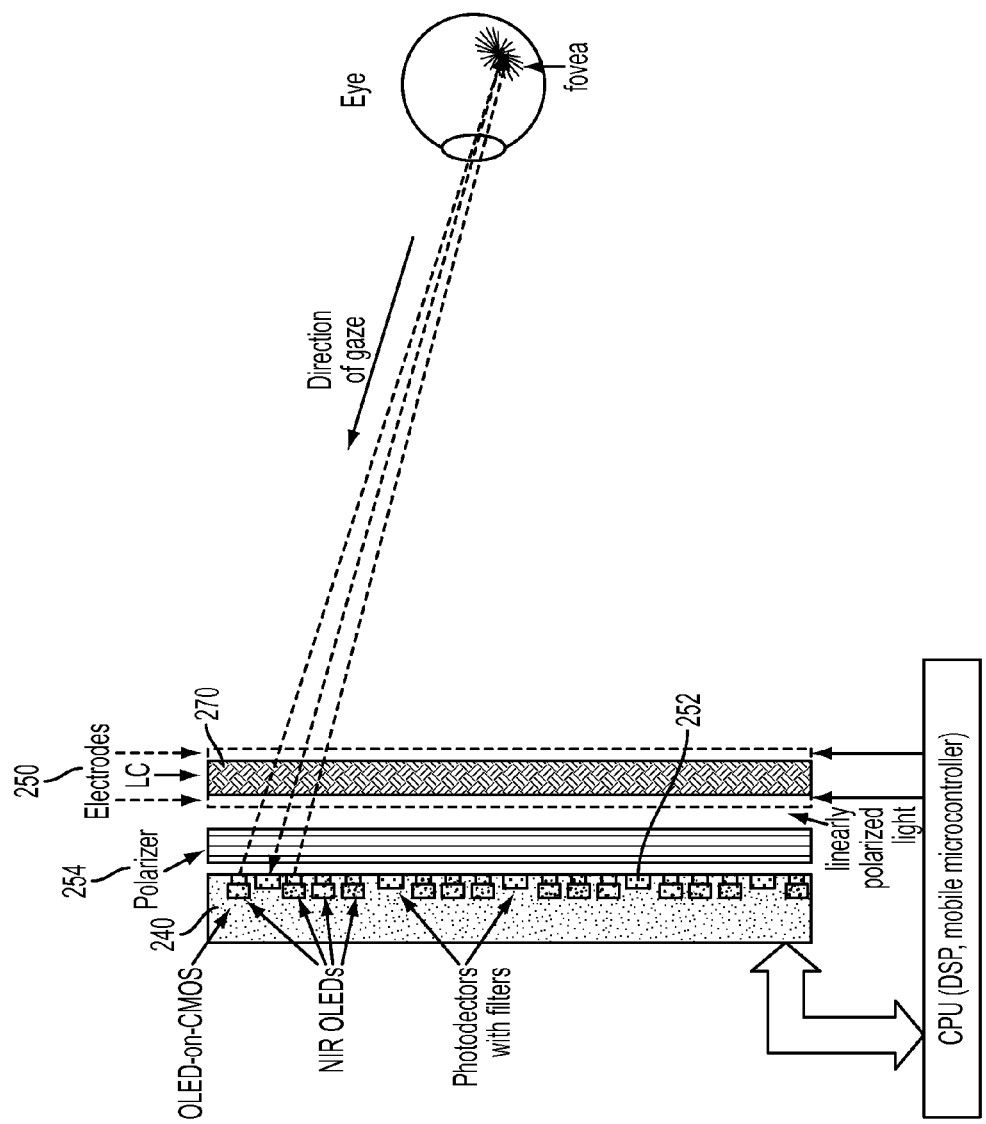
FIG. 33 shows the OLED-on-CMOS microdisplay with integrated emitters-detectors in relation to an eye.

In FIGS. 32 and 33, an eye tracking and gaze fixation detection system 100 includes a display 146 that is adapted to be viewed by the subject and the electronically scannable optical illumination system 102 and the optical detection system 104 are integrated into a viewing region of the display 146. In recent years, new devices have been developed, integrating both emitters and sensors on a single device. Among them, for example, is the OLED-on-CMOS "bidirectional" technology developed by Fraunhoffer COMEDD, Dresden, Germany, mainly for microdisplays disclosed in "NIR Active OLEDs and Their Integration in CMOS Micro-Displays," Fraunhofer COMEDD (available at http://www.comedd.fraunhofer.de/content/dam/comedd/common/products/COMEDD/nir-oled-e.pdf), the content of which is hereby incorporated by reference in its entirety. This technology integrates highly efficient, low voltage organic light emitting diodes (OLEDs) and photodiodes (with their corresponding amplifiers and analog-to-digital converters) on a CMOS-substrate, to combine display and camera functionality. One targeted application is for microdisplays that are also capable of tracking the eye by capturing the red reflex from the pupil or the corneal light reflex when illuminating the eye with an infrared light source. This method does not follow the fovea, and is imprecise, as are most eye trackers that employ the pupillary red reflex or an infrared reflection from the surface of the eye.

The method proposed here is based on the already known OLED-on-CMOS technology summarized above, but employs the property of the fovea to change the polarization state of light. Newer OLED-on-CMOS chips contain OLEDs that can radiate in red, green, blue (RGB) and near-infrared (NIR) spectral range. Typically, OLED-on-CMOS devices contain significantly more OLEDs than nested photodiodes, as shown on the figures below. For the purpose of this application, only NIR OLEDs are used. With the design being proposed here, the normal display operation (in the usual RGB mode) is periodically interrupted, whereby the RGB OLEDs are turned off, and the NIR OLEDs are fired in succession, one at a time. During each firing, signals from all, or from only adjacent photodetectors are acquired. After the foveal region is fully scanned by all NIR OLEDs, the location of the fovea and hence the direction of gaze are calculated using the same mechanism as described earlier in this description.

FIG. 33 shows an embodiment with a polarizer 254 and electrodes 250. A role of the polarizer is to convert the light coming from the OLEDs into polarized light, and also to analyze and detect changes in polarization after reflection from the region of the fovea being scanned each time. In addition to the polarizer 254, a combination of an LC 270 and two transparent electrodes may be added (optional). Depending on the voltage applied to the electrodes, the LC molecules untwist and thus change their birefringence, functioning as a controllable retarder. This helps to optimize the system and maximize the birefringence signal obtained.

Figure 34:
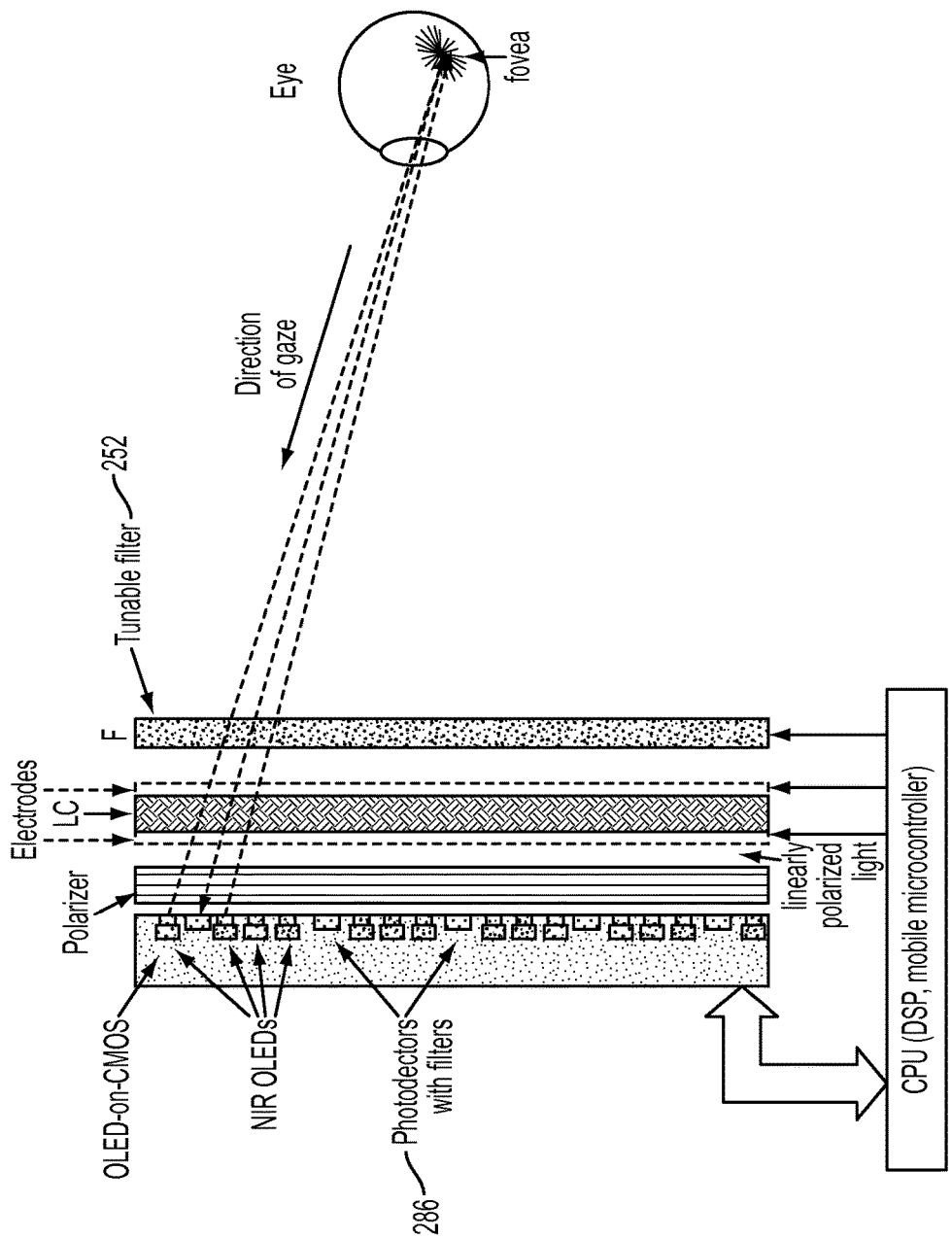
FIG. 34 shows the OLED-on-CMOS microdisplay with integrated emitters-detectors in relation to an eye with a tunable filter.

It is desirable to use an OLED-on-CMOS device that has a microscopic interference filter 286 in front of each photodetector, passing only NIR light in the spectral range of the NIR OLED emitters. Alternatively, a tunable optical filter 252 may be used, as shown in FIG. 34. This filter passes either all visible wavelengths during normal operation of the OLED display, or passes only the NIR spectral range during measurement.

Some features of some embodiments:
1. A method for estimating the direction of gaze when a person is looking at a screen or control board located up to 45 cm from the eyes. The method uses reflections from different parts of the eye, mainly from the retina and the cornea. No optical parts are placed between the face and the screen (or control board). The method rather uses the eye's own optics, and employs no moving parts.

2. The method further uses polarized light and the property of ocular media to change the polarization states of light.
3. A class of emitter-receiver transducers is devised for emitting polarized near-infrared (NIR) light toward the eyes, and measuring the polarization changes in the returning light. In contrast to other differential polarization measurement systems, these transducers can measure returning light of changed polarization without losses that are usually incurred by a non-polarizing beam splitter used to introduce the source of light into the common light path.
4. A transducer described in 3, consisting of a laser diode, a photodetector sensor, a filter and a polarizer.
5. A transducer described in 3, consisting of a laser diode, a photodetector sensor, a filter, a 90° liquid crystal (LC) polarization rotator, typically a twisted nematic (TN) device, and a polarizer.
6. A transducer described in 3, consisting of a fiber-coupled laser diode, a photodetector sensor, a filter and a polarizer.
7. A transducer described in 3, consisting of a fiber-coupled laser diode, a photodetector sensor, a filter, a liquid crystal (LC) polarization rotator, typically a twisted nematic (TN) device, and a polarizer.
8. A transducer described in 3, consisting of a laser diode or any other source of polarized light, a miniature polarizing beam splitter, and two sensors, one of which has a small hole in its center, to pass the incoming polarized light. The retro-reflected light is decomposed into its two orthogonal components (s- and p-), and is detected by the two sensors.
9. A combination of multiple laser-diode-based transducers, where the laser diodes are part of the transducer, and are activated sequentially, one at a time.
10. A combination of multiple laser-diode-based transducers, where the laser diodes are fiber-coupled to the transducer, and are activated sequentially, one at a time.
11. A combination of multiple laser-diode-based transducers, where one laser diode is fiber-coupled to multiple transducers via an optical switch (multiplexer), so that the transducers are activated sequentially, one at a time.
12. An integrated configuration of an edge-emitter laser diode, combined with a photodetector, as part of the transducer described in 3.
13. An integrated configuration of a vertical cavity surface emitting laser, combined with a photodetector, as part of the transducer described in 3.
14. A method of detecting the direction of gaze where multiple transducers as described in 3 are positioned at the edge of a screen or control board, sending polarized light toward the eyes, and measuring polarization changes in the retro-reflected light.
15. A method of measuring the polarization changes of the light reflected from the retina of at least one eye and passing through the cornea by means of a liquid crystal polarization rotator.
16. A method of estimating the direction of gaze using light reflected from a retina of at least one eye and captured by multiple detectors, based on a linear algebra solution, after calibration.
17. A method of estimating the direction of gaze using light reflected from the eyes and captured by multiple detectors, based on a neural network, after calibration.
18. A class of no-moving-part central fixation monitors using multiple stationary light sources (emitters) arranged typically (but not necessarily) in a circular pattern and activated in succession. The light returning from the foveal region of the retina is partially diverted through a beam splitter to a sensor on which there is a matching, individually accessible area, conjugate to one emitter. Each time an emitter is flashed, light of changed polarization is reflected by the corresponding foveal region and is measured by the corresponding area on the sensor.
19. A no-moving-part central fixation monitor, as described in 18, using multiple laser diodes, a beam splitter, an interference filter, a computer controlled liquid crystal polarization rotator, a polarizer, and a segmented sensor optically conjugate to the emitters with respect to the eye.
20. A no-moving-part central fixation monitor, as described in 18, using multiple NIR light emitting diodes (LEDs), a polarizer, a beam splitter, an interference filter, a computer controlled liquid crystal polarization rotator, a second polarizer, and a segmented sensor optically conjugate to the emitters with respect to the eye.
21. A no-moving-part central fixation monitor, as described in 18, using multiple laser diodes, a beam splitter, an interference filter, a computer controlled liquid crystal polarization rotator, a polarizer, and a camera sensor (CCD or CMOS) optically conjugate to the emitters with respect to the eye.
22. A no-moving-part central fixation monitor, as described in 18, using a quarter wave plate (QWP), sending circularly polarized light into the eye. This design reduces interference caused by specular reflections, and variability among eyes caused by differences in corneal birefringence.
23. A method of focusing the returned light onto the sensor array by means of an electrically controlled deformable lens, controlled by a computer in a closed loop.
24. A method of estimating the level of defocus of the light returning from the retina based on the size of the spot produced by a sensor, or by many sensors, as captured by the sensor array mentioned in 19.
25. A no-moving-part central fixation monitor, as described in 18, using a method for compensation of individual corneal birefringence by means of a variable liquid crystal retarder in the measurement path, controlled by the CPU. Before the actual measurement, with the test subject fixating at a target, the system keeps taking measurements while changing the retardance—first in larger steps, then in smaller, until the measured amplitude is maximized.
26. A no-moving-part central fixation monitor, as described in 18, using a method of rotating the polarization plane of the input light during data acquisition, where the polarization orientation is adjusted for every source before acquiring data from the area on the sensor that matches it. The light sources are activated at a speed $f_{scan}$ whereas the polarization is spun at a speed $x*f_{scan}$. Spectral analysis involving the output at n interrogating points then reveals the characteristic frequencies.
27. A no-moving-part central fixation monitor, as described in 18, achieving differential polarization detection by means of a polarizing beam splitter and two sensors measuring simultaneously the p- and the s-component respectively.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. An eye tracking and gaze fixation detection system, comprising:
   an electronically scannable optical illumination system arranged to emit polarized near-infrared (NIR) light to at least a portion of a retina in an eye of a subject;
   an optical detection system arranged in an optical path of said NIR light after being reflected from the retina of the eye of the subject, said optical detection system providing a detection signal; and
   a signal processing system configured to communicate with the optical detection system to receive said detection signal,
   wherein the optical illumination system is configured to emit the polarized NIR light to illuminate at least a portion of a scanning path,
   wherein said scanning path is a spatially closed loop across a portion of said retina in said eye of said subject that repeats periodically over time, and
   wherein the signal processing system is configured to determine at least one of a gaze direction and a gaze fixation based on the detection signal.

2. The eye tracking and gaze fixation detection system of claim 1, wherein the electronically scannable optical illumination system comprises a plurality of emitters that are electronically addressable to emit in a timed sequence corresponding to portions of said scanning path.

3. The eye tracking and gaze fixation detection system of claim 2, wherein the optical detection system comprises a plurality of polarization-sensitive detectors arranged at least one of substantially coincident with or optically conjugate with a corresponding one of the plurality of emitters to detect the at least one polarization component of reflected near-infrared light from the retina of the eye of the subject.

4. The eye tracking and gaze fixation detection system according to claim 3, wherein the optical detection system comprises a liquid crystal polarization rotator,
   wherein the liquid crystal polarization rotator is configured to rotate the detected polarization component.

5. The eye tracking and gaze fixation detection system of claim 3, wherein the plurality of emitters and the plurality of detectors are positioned outside a periphery of a screen that is adapted for the subject to gaze at.

6. The eye tracking and gaze fixation detection system according to claim 3, wherein the plurality of detectors comprises an image sensor array.

7. The eye tracking and gaze fixation detection system of claim 2, wherein each of the plurality of emitters comprises a laser diode.

8. The eye tracking and gaze fixation detection system according to claim 7, wherein each of the plurality of laser diodes is one of at least an edge-emitting laser diode or a vertical cavity surface emitting laser diode.

9. The eye tracking and gaze fixation detection system according to claim 7, wherein said electronically scannable optical illumination system further comprises a liquid crystal polarization rotator arranged to rotate the plane of polarization of the light from said plurality of laser diodes to enhance said detection signal.

10. The eye tracking and gaze fixation detection system according to claim 7, wherein said electronically scannable optical illumination system further comprises a plurality of optical fibers, and
    wherein each optical fiber of said plurality of optical fibers is optically coupled to a corresponding one of said plurality of laser diodes.

11. The eye tracking and gaze fixation detection system according to claim 2, wherein the optical detection system comprises a plurality of photodetectors arranged to substantially surround each of the plurality of emitters in a plane substantially common to the location of both the emitters and the detectors.

12. The eye tracking and gaze fixation detection system according to claim 2, wherein the electronically scannable optical illumination system comprises a laser diode coupled to an optical multiplexer, and
    wherein the optical multiplexer is optically coupled to each of the plurality of emitters.

13. The eye tracking and gaze fixation detection system according to claim 2, wherein each of the plurality of emitters comprises a light-emitting diode, and
    wherein the electronically scannable optical illumination system further comprises a polarizer disposed in an optical path between the emitters and the subject.

14. The eye tracking and gaze fixation detection system according to claim 13, wherein the electronically scannable optical illumination system comprises an optical multiplexer that is optically coupled to each of the plurality of emitters.

15. The eye tracking and gaze fixation detection system of claim 2, wherein said timed sequence of said plurality of emitters is determined by electronically addressable liquid crystal shutters arrayed before said emitters that allow emission of the NIR light of the emitter through the electronically addressable liquid crystal shutters in said sequence.

16. The eye tracking and gaze fixation detection system of claim 1, wherein the electronically scannable optical illumination system comprises an emitter that is arranged to continuously emit NIR light in a timed sequence, and said timed sequence of emission of said emitter being determined by electronically addressable liquid crystal shutters arrayed before said emitter that allows emission of the NIR light of the emitter through the electronically addressable liquid crystal shutters in said sequence.

17. The eye tracking and gaze fixation detection system of claim 1, wherein said electronically scannable optical illumination system comprises:
    a digital micromirror device comprising a plurality of micromirrors, and
    an emitter of NIR light arranged to illuminate at least a portion of said digital micromirror device,
    wherein the plurality of micromirrors are configured to have electronically addressable ON and OFF states to provide a timed sequence of NIR light corresponding to at least a portion of said scanning path.

18. The eye tracking and gaze fixation detection system of claim 1, further comprising a display that is adapted to be viewed by the subject,
    wherein said electronically scannable optical illumination system and said optical detection system are integrated into a viewing region of said display.

19. The eye tracking and gaze fixation detection system according to claim 1, further comprising a variable liquid crystal retarder arranged in the optical path of the NIR light from the electronically scannable optical illumination system after being reflected from the object of interest prior to being detected by the optical detection system.

20. The eye tracking and gaze fixation detection system according to claim 19, wherein the variable liquid crystal retarder is electrically controllable by a central processing unit.

21. The eye tracking and gaze fixation detection system according to claim 1, further comprising an interference filter arranged in the optical path of the NIR light from the electronically scannable optical illumination system after being reflected from the eye of the subject prior to being detected by the optical detection system.

22. The eye tracking and gaze fixation detection system according to claim 1, wherein said electronically scannable optical illumination system and said optical detection system comprise a polarization-sensitive optical transducer, said polarization-sensitive optical transducer comprising:
 a source of polarized light that has an end portion arranged to project the polarized light;
 a photodetector that surrounds the source of polarized light and that is in a substantially same plane as the end portion of the source of polarized light,
 wherein the photodetector senses light from said source of polarized light when the light strikes a polarization-changing object and is back-reflected toward said source and surrounding photodetector,
 wherein said polarization-sensitive optical transducer is configured to detect a polarization state of the back-reflected light, and
 wherein the polarization-sensitive optical transducer provides information about the polarization changing properties of said polarization-changing object based on the detected polarization state.

23. A polarization-sensitive optical transducer comprising:
 a source of polarized light that has an end portion arranged to project the polarized light;
 a photodetector that surrounds the source of polarized light and that is in a substantially same plane as the end portion of the source of polarized light,
 wherein the photodetector senses light from said source of polarized light when the light strikes a polarization-changing object and is back-reflected toward said source and surrounding photodetector,
 wherein said polarization-sensitive optical transducer is configured to detect a polarization state of the back-reflected light, and
 wherein the polarization-sensitive optical transducer provides information about the polarization changing properties of said polarization-changing object based on the detected polarization state.

24. The polarization-sensitive optical transducer of claim 23, wherein the photodetector comprises a linear polarizer.

25. The polarization-sensitive optical transducer of claim 24, wherein said photodetector further comprises a polarization rotator that is configured to rotate the polarization orientation of the back-reflected light to at least one meridional position.

26. The polarization-sensitive optical transducer of claim 23, wherein said source of polarized light comprises a pigtail laser diode having a polarization-preserving fiber that extends through a hole in said surrounding photodetector.

27. The polarization-sensitive optical transducer of claim 23, wherein said surrounding photodetector further comprises a polarizing beam splitter and two photodetectors arranged for differential polarization measurement of the polarization state of said back-reflected light.

28. The polarization-sensitive optical transducer of claim 27, wherein:
 one of the two photodetectors is a first-encountered photodetector, and one of the two photodetectors is a second-encountered photodetector, wherein the back-reflected light is detected by the first-encountered photodetector before the second-encountered photodetector,
 the first-encountered photodetector is tilted in relation to the plane of the end portion of the source of polarized light, and
 said polarizing beam splitter comprises thin-film layers deposited directly onto a surface of the first-encountered photodetector such that the p-component of the polarized light passes through the thin-film layers and is absorbed by the first-encountered photodetector, and the s-component of the polarized light is reflected by the thin film layers to be absorbed by the second-encountered photodetector.

* * * * *